(12) United States Patent
Cheng et al.

(10) Patent No.: US 7,193,088 B2
(45) Date of Patent: Mar. 20, 2007

(54) IRIDIUM COMPLEXES AS LIGHT EMITTING MATERIALS AND ORGANIC LIGHT EMITTING DIODE DEVICE

(75) Inventors: Chien-Hong Cheng, Hsinchu (TW); Ruey-Min Chen, Tainan County (TW); Hong-Ru Guo, Tainan County (TW); Jun-Wen Chung, Tainan County (TW)

(73) Assignees: Chi Mei Optoelectronics, Tainan County (TW); National Tsing Hua University, Hsinchu (TW)

( * ) Notice: Subject to any disclaimer, the term of this patent is extended or adjusted under 35 U.S.C. 154(b) by 192 days.

(21) Appl. No.: 10/992,594

(22) Filed: Nov. 17, 2004

(65) Prior Publication Data
US 2005/0116626 A1 Jun. 2, 2005

(30) Foreign Application Priority Data
Nov. 18, 2003 (TW) ............... 92132297 A

(51) Int. Cl.
*C07F 15/00* (2006.01)
*H01J 1/62* (2006.01)
*H01J 63/04* (2006.01)

(52) U.S. Cl. .............. 548/103; 548/108; 428/690; 428/917; 313/504

(58) Field of Classification Search ............. 548/103, 548/108; 428/690, 917; 313/504
See application file for complete search history.

(56) References Cited

U.S. PATENT DOCUMENTS

| 6,687,266 B1 | 2/2004 | Ma et al. | |
|---|---|---|---|
| 6,936,716 B1* | 8/2005 | Lin | 546/2 |
| 2005/0008895 A1* | 1/2005 | Takada et al. | 428/690 |
| 2006/0008670 A1* | 1/2006 | Lin et al. | 428/690 |

OTHER PUBLICATIONS

Huang et al., Chemistry of Materials, 16(12), 2480-2488, 2004.*

* cited by examiner

*Primary Examiner*—Fiona T. Powers
(74) *Attorney, Agent, or Firm*—Finnegan, Henderson, Farabow, Garrett & Dunner, L.L.P.

(57) ABSTRACT

Phosphorescent iridium complexes having Formula I or Formula II:

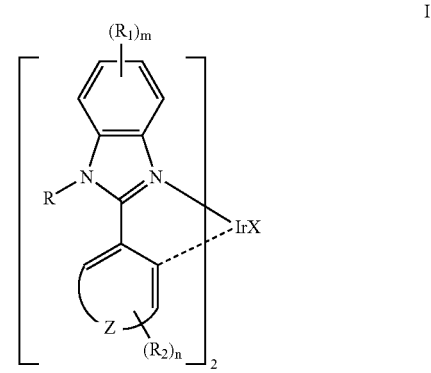

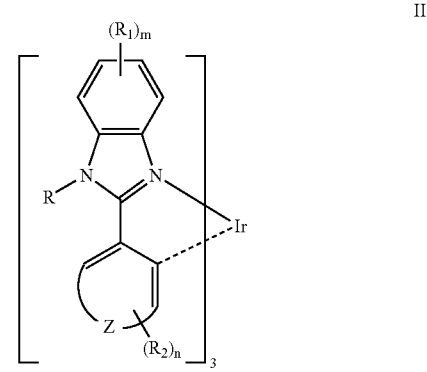

wherein X is chosen from a monoanionic bidentate ligand; Z is chosen from an atomic group wherein Z together with the buta-1,3-diene to which Z is attached form an aryl group or heteroaryl group; R, $R_1$, and $R_2$ are independently chosen from a hydrogen atom or a substituent; m is an integer from 0 to 4; and n is an integer from 0 to the maximum number of possible substituents on Z, are disclosed. Light emitting devices using the phosphorescent iridium complexes are also disclosed.

39 Claims, 8 Drawing Sheets

IRIDIUM COMPLEXES AS LIGHT EMITTING MATERIALS AND ORGANIC LIGHT EMITTING DIODE DEVICE This application claims the right to foreign priority based on Patent Application No. 92132297, filed Nov. 18, 2003, in Taiwan, which is incorporated herein by reference.

FIELD

This disclosure relates to iridium complexes and light emitting devices comprising iridium complexes as phosphorescent bodies. More particularly, the present disclosure relates to iridium complexes and light emitting devices using iridium complexes that can be used, for example, in display elements, displays, backlights, illumination light sources, and the like.

INTRODUCTION

Electroluminescent ("EL") devices using organic luminescent materials are being actively researched recently because of the ability of displays fabricated using EL devices to exhibit wider viewing angles and faster response times than conventional liquid crystal displays. More particularly, flat panel displays fabricated using EL devices made from organic luminescent materials are expected to use spontaneous light emission. Furthermore, EL devices using organic luminescent materials can exhibit advantages such as low power consumption, high brightness, and light and thin design, which can be useful in consumer electronic devices such as digital cameras, personal digital assistants, and videophones. An example of a light-emitting device is an organic light-emitting diode (OLED). An OLED device can include an organic thin film containing a luminescent material formed between an optically transparent anode and a metallic cathode which emits light when an electric current is applied. To produce a full-color EL display panel using OLEDs, it is useful to have efficient red, green, and blue EL materials with appropriate chromaticity and luminance efficiency.

OLEDs exhibiting high luminance efficiency can be fabricated using electroluminescent materials containing heavy metal complexes. For example, electroluminescent materials comprising complexes of platinum, iridium, and osmium can be used to form OLEDs with high luminance efficiency, with the iridium complexes exhibiting the highest efficiency. Iridium complexes exhibiting high luminance efficiency typically have an octahedral structure with the iridium center in a +3 oxidation state. The mechanism of luminance emission of these iridium complexes is based on a triplet-$^3$MLCT (metal to ligand charge transfer) transition between the metal and ligand, or a triplet-$^3\pi$-$\pi$* ligand-centered luminescence. The strong spin-orbit coupling of the heavy metal complexes produces high phosphorescence efficiency.

SUMMARY

Certain aspects of the present disclosure provide phosphorescent iridium complexes that can be used in a light emitting layer of a light emitting device. Light emitting devices comprising at least one iridium complex disclosed herein exhibit high brightness, high external quantum efficiency, high current efficiency, and excellent CIE coordinates.

A second aspect of the present disclosure provides phosphorescent iridium complexes that can be used in a light emitting layer of a light emitting device capable of emitting light having a peak wavelength ranging from the blue to green regions of the electromagnetic spectrum.

A third aspect of the present disclosure provides six-coordinated octahedral phosphorescent iridium complexes formed from three bidentate ligands. Phosphorescent iridium complexes disclosed herein have structural Formula (I) or Formula (II):

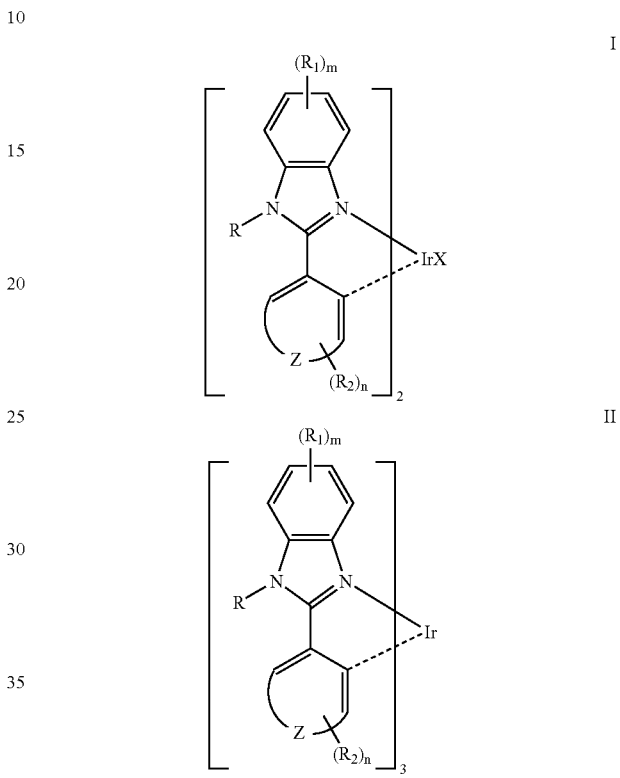

wherein X is chosen from a monoanionic bidentate ligand; Z is chosen from a group wherein Z together with the buta-1,3-diene group to which Z is attached form an aryl group or a heteroaryl group; R, $R^1$ and $R^2$ are independently chosen from H, halogen, $C_1$–$C_{20}$ alkyl, $C_2$–$C_{20}$ alkenyl, $C_2$–$C_{20}$ alkynyl, halogen-substituted $C_1$–$C_{20}$ alkyl, $C_1$–$C_{20}$ alkoxy, $C_1$–$C_{20}$ substituted amino, $C_1$–$C_{20}$ acyl group, $C_1$–$C_{20}$ ester, $C_1$–$C_{20}$ amide, aryl, halogen-substituted aryl, halogen-substituted alkenyl, haloalkyl-substituted aryl, haloalkyl-substituted alkenyl, aryl-substituted $C_1$–$C_{20}$ alkyl, cyano, and nitro; m is an integer from 0 to 4; and n is an integer from 0 to the maximum number of possible substituents on Z.

A fourth aspect of the present disclosure provides light emitting devices made using at least one compound of Formula (I) or Formula (II).

Additional embodiments of the invention are set forth in the description which follows, or may be learned by practice of the invention.

DEFINITIONS USED IN THE PRESENT DISCLOSURE

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements. At the very least, and not as an attempt to limit the application of the doctrine of equivalents to the scope of the claims, each numerical parameter as set forth in the claims should at least be construed in light of the number of reported significant digits and by applying ordinary rounding techniques.

"Acyl" refers to a radical —C(O)R', where R' is hydrogen or alkyl, as defined herein. In certain embodiments, an acyl group has from 1 to 20 carbon atoms.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkoxy" refers to a radical —OR' where R' represents an alkyl group, as defined herein. Representative examples include, but are not limited to, methoxy, ethoxy, propoxy, butoxy, cyclohexyloxy, and the like. In certain embodiments, an alkoxy group has from 1 to 20 carbon atoms.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1, 3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms. In other embodiments, an alkyl group comprises from 1 to 6 carbon atoms, and is referred to as a lower alkyl group.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Amide" refers to the group —C(O)NR'R" where R' and R" are independently chosen from hydrogen, and alkyl. In certain embodiments, R' and R" are independently chosen from an alkyl group having from 1 to 20 carbon atoms.

"Amino acid" refers to a naturally occurring or synthetic compound having an amino group and a carboxyl group and a side chain attached to an α carbon atom and which can form a polypeptide and/or protein.

"Aryl" refers to a monovalent aromatic hydrocarbon group derived by the removal of one hydrogen atom from a single carbon atom of a parent aromatic ring system. Examples of aryl groups include, but are not limited to, groups derived from phenyl, naphthyl, diphenyl, anthryl, pyrenyl, phenanthryl, and fluorene, and the like. In certain embodiments, an aryl group can comprise from 6 to 21 carbon atoms.

"Aryl-substituted alkyl" refers to an acyclic alkyl group in which one of the hydrogen atoms bonded to a carbon atom, typically a terminal or $sp^3$ carbon atom, is replaced with an aryl group. Examples of aryl-substituted alkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenyle-than-1-yl and the like. In certain embodiments, the alkyl portion of the aryl substituted alkyl includes from 1 to 20 carbon atoms. The aryl portion of an aryl substituted alkyl can be any aryl group as defined herein.

"Cyano" refers to the radical —CN.

"Ester" refers to a radical —C(O)OR where R represents hydrogen or an alkyl group, as defined herein. In certain embodiments, an ester group has from 2 to 20 carbon atoms.

"Halogen" refers to a fluoro, chloro, bromo, or iodo group.

"Halogen-substituted alkyl" refers to an alkyl group as defined herein, in which one or more hydrogen atoms are substituted with a halogen.

"Halogen-substituted aryl" refers to an aryl group as defined herein, in which one or more hydrogen atoms are substituted with a halogen.

"Halogen-substituted alkenyl" refers to an alkenyl group as defined herein, in which one or more hydrogen atoms are substituted with a halogen.

"Haloalkyl-substituted aryl" refers to an aryl group as defined herein, in which one or more hydrogen atoms are substituted with a halogen-substituted alkyl group.

"Haloalkyl-substituted alkenyl" refers to an alkenyl group as defined herein, in which one or more hydrogen atoms are substituted with a halogen-substituted alkyl group.

"Heteroaryl" refers to a monovalent heteroaromatic group derived by the removal of one hydrogen atom from a single atom of a parent heteroaromatic ring system. Examples of heteroaryl groups include, but are not limited to, groups derived from benzofuran, thiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, and phenanthroline, and the like. In certain embodiments, the heteroaryl group can be between 5 to 20 membered heteroaryl, such as, for example, a 5 to 10 membered heteroaryl.

"Maximum possible number of substituents on Z" refers to number of substituents that can be substituted on Z. Z is an atomic group attached to a buta-1,3-diene group. The maximum number of possible substituents on Z will depend on valency of the atoms comprising Z. For example, when Z together with the buta-1,3-diene group to which Z is attached form a benzene ring, the maximum number of possible substituents will be 4; when Z together with the buta-1,3-diene group to which Z is attached form a naphthalene ring, the maximum number of possible substituents will be 6; and when Z together with the buta-1,3-diene group to which Z is attached form a benzofuran ring, the maximum number of substituents will be 4.

"Nitro" refers to the radical —$NO_2$.

"Substituted amino" refers to a radical —NR'R" where R' and R" are independently chosen from hydrogen, and alkyl. In certain embodiments, R' and R" are independently chosen from an alkyl group having from 1 to 20 carbon atoms.

DESCRIPTION OF THE DRAWINGS

Other objects, advantages, and novel features of the invention will become more apparent from the following detailed description when taken in conjunction with the accompanying drawings.

DESCRIPTION

Figure 1:
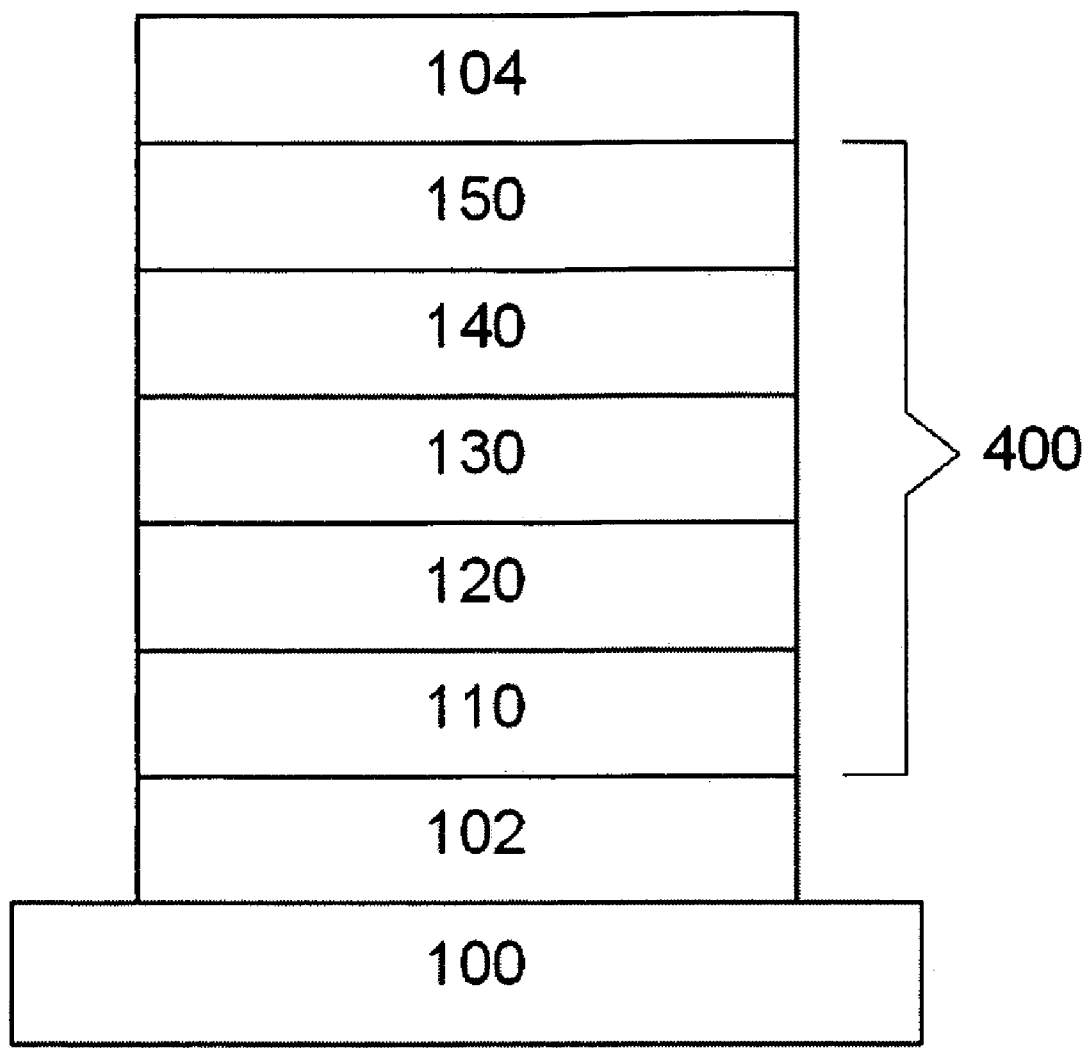
FIG. 1 is a schematic sectional view of an organic light emitting diode device according to certain embodiments.

The present disclosure is generally directed to light-emitting materials comprising at least one phosphorescent iridium complex. Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In the specification and the appended claims, the singular forms "a," "an," and "the" include plural reference unless the context clearly dictates otherwise.

According to certain embodiments, a phosphorescent iridium complex is a six-coordinated octahedral complex formed from three bidentate ligands of Formula (I) or Formula (II):

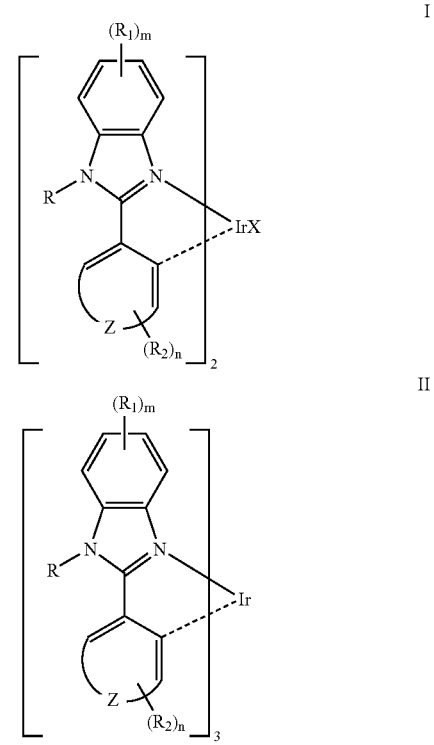

wherein X is chosen from a monoanionic bidentate ligand; Z is chosen from an atomic group wherein Z together with the buta-1,3-diene group to which Z is attached form an aryl group or a heteroaryl group; R, $R_1$, and $R_2$ are independently chosen from H, halogen, $C_1$–$C_{20}$ alkyl, $C_2$–$C_{20}$ alkenyl, $C_2$–$C_{20}$ alkynyl, halogen-substituted $C_1$–$C_{20}$ alkyl, $C_1$–$C_{20}$ alkoxy, $C_1$–$C_{20}$ substituted amino, $C_1C_{20}$ acyl group, $C_1$–$C_{20}$ ester, $C_1$–$C_{20}$ amide, aryl, halogen-substituted aryl, halogen-substituted alkenyl, haloalkyl-substituted aryl, haloalkyl-substituted alkenyl, aryl-substituted $C_1$–$C_{20}$ alkyl, cyano, and nitro; m is an integer from 0 to 4; and n is an integer from 0 to the maximum number of possible substituents on Z.

In certain complexes of Formula (I) or Formula (II), $R_1$, $R_2$ and $R_3$ are independently chosen from H, halogen (e.g., fluorine, chlorine, bromine, or iodine), $C_1$–$C_{20}$ alkyl (e.g., methyl, ethyl, butyl, or cyclohexyl), $C_2$–$C_{20}$ alkenyl, $C_2$–$C_{20}$ alkynyl, halogen-substituted $C_1$–$C_{20}$ alkyl (such as trifluoromethyl), $C_1$–$C_{20}$ alkoxy, $C_1$–$C_{20}$ substituted amino, $C_1$–$C_{20}$ acyl, $C_1$–$C_{20}$ ester, $C_1$–$C_{20}$ amide, aryl, halogen-substituted aryl, halogen-substituted alkenyl, haloalkyl-substituted aryl, haloalkyl-substituted alkenyl, aryl-substituted $C_1$–$C_{20}$ alkyl (e.g., phenylmethyl), cyano, and nitro.

In certain complexes of Formula (I) or Formula (II), R is chosen from H, $C_1$–$C_{20}$ alkyl, aryl, aryl-substituted $C_1$–$C_{20}$ alkyl, halogen-substituted aryl, haloalkyl-substituted aryl, haloalkyl-substituted alkenyl, and halogen-substituted alkenyl.

In certain complexes of Formula (I) or Formula (II), R is chosen from H, $C_1$–$C_{20}$ alkyl, aryl, aryl-substituted $C_1$–$C_{20}$ alkyl, halogen-substituted aryl, haloalkyl-substituted aryl, haloalkyl-substituted alkenyl, and halogen-substituted alkenyl, and $R_1$ is chosen from H, and $C_1$–$C_{20}$ alkyl.

In certain complexes of Formula (I) or Formula (II), R is chosen from H, $C_1$–$C_{20}$ alkyl, aryl, aryl-substituted $C_1$–$C_{20}$ alkyl, halogen-substituted aryl, haloalkyl-substituted aryl, haloalkyl-substituted alkenyl, and halogen-substituted alkenyl, $R_1$ is chosen from H, and $C_1$–$C_{20}$ alkyl, and $R_2$ is chosen from H, halogen, $C_1$–$C_{20}$ alkyl, halogen-substituted $C_1$–$C_{20}$ alkyl, and $C_1$–$C_{20}$ alkoxy.

In certain complexes of Formula (I) or Formula (II), m is an integer from 0 to 4, and n is an integer from 0 to the maximum number of possible substituents on Z.

In certain complexes of Formula (I) or Formula (II), Z together with the buta-1,3-diene group to which Z is attached form an aryl group chosen from phenyl, naphthyl, diphenyl, anthryl, pyrenyl, phenanthryl, and fluorene.

In certain complexes of Formula (I) or Formula (II), Z together with the buta-1,3-diene group to which Z is attached form a heteroaryl group chosen from benzofurane, thiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, and phenanthroline.

In certain complexes of Formula (I) or Formula (II), X is chosen from acetylacetonate, an amino acid anion, salicylaldehyde anion, 2-picolinate, 8-hydroxyquinoline anion, and iminoacetonate.

In certain complexes of Formula (I) or Formula (II), X is acetylacetonate.

In certain complexes of Formula (I) or Formula (II), a phosphorescent iridium complex is chosen from Formula II-1, II-2, II-3, II-4, II-5, II-6, II-7, II-8, II-9, II-10, II-11, II-12, and II-13:

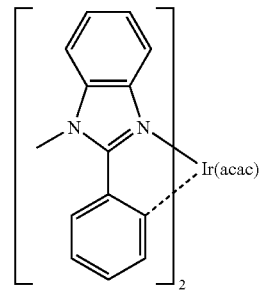

II-1

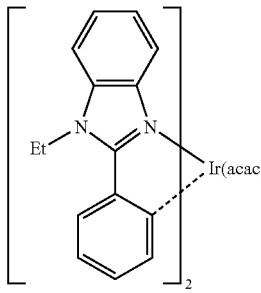

II-2

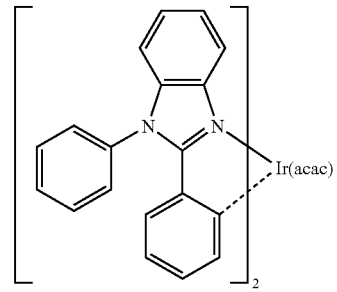

II-3

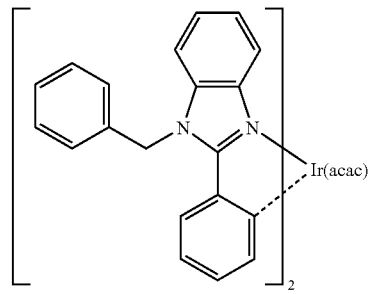

II-4

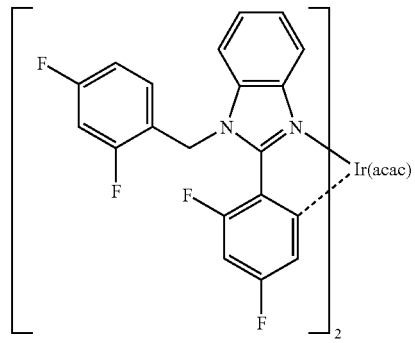

II-5

-continued
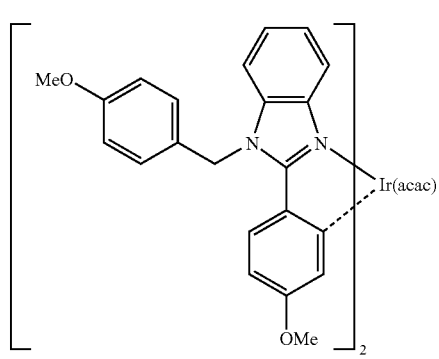
II-6
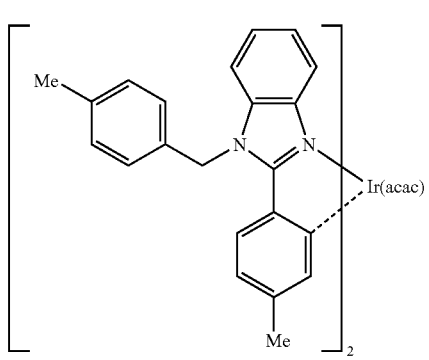
II-7
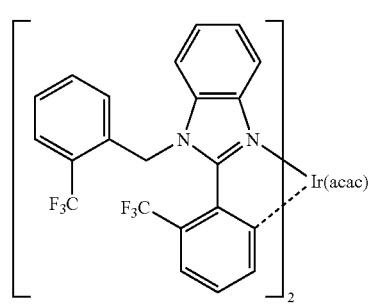
II-8
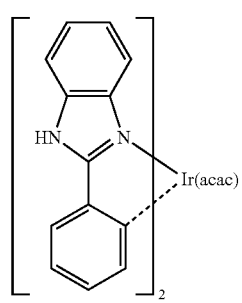
II-9
-continued
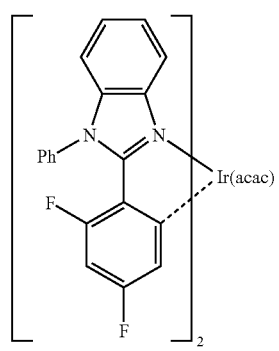
II-10
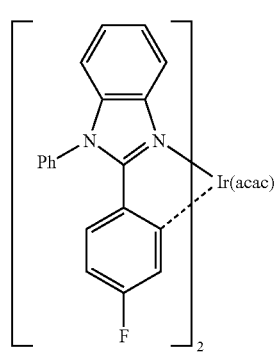
II-11
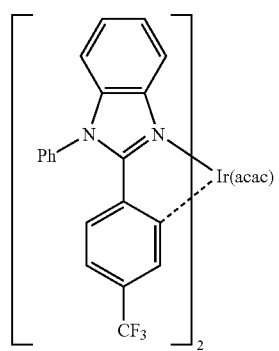
II-12
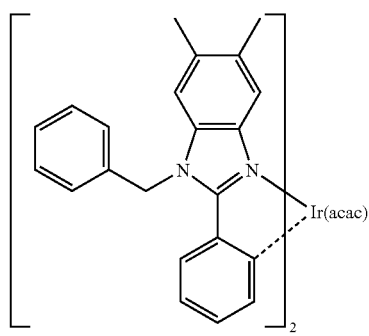
II-13

Phosphorescent iridium complexes of the present disclosure can be used to form a luminescent layer in an OLED device. An OLED device of the present disclosure can comprise a light-emitting layer, or a plurality of organic compound layers including the light-emitting layer disposed between a pair of electrodes comprising an anode and a cathode. In certain embodiments, a light-emitting device can comprise a luminescent layer comprising at least one phosphorescent iridium complex of the present disclosure disposed between an electron transporting layer and a hole transporting layer. A light-emitting device of the present disclosure is not specifically limited in its system, driving method, and/or form of utilization so far as it comprises at least one compound of the present disclosure. An example of a light-emitting device is an OLED device. Thus, in certain embodiments, a phosphorescent iridium complex of the present disclosure can be used as a phosphorescent material in an OLED device.

The structure of OLED devices can be classified as bottom emission devices, and top emission devices. A bottom emission device can have an anode made of a transparent material such as indium tin oxide (ITO) and a cathode made of an opaque or reflective low work function metal, such as Al or a Mg:Ag alloy, wherein light is emitted through the transparent anode. A top emission device can have an anode made of an opaque or reflective metal, such as Al/Ni or Al/TiO, and a cathode made of a low work function metal such as Ca, Al, a Mg:Ag alloy, or ITO, which is transparent for small thickness, wherein light is emitted through the transparent cathode.

A bottom emission device can be manufactured using the following method. A glass substrate is used to form the device. A transparent anode, a hole injection modification layer (optional), a hole transporting layer, a light-emitting layer, a hole blocking layer, an electron transporting layer, an election injection layer of potassium fluoride(optional), and a cathode are sequentially formed on the glass substrate. Before subsequent layers are formed, the glass substrate and anode is cleaned in commercially available detergent solution and organic solvent, and treated using a UV-ozone cleaner.

FIG. 1 shows a bottom emission OLED device according to certain embodiments of the disclosure. The dimensions shown in FIG. 1 do not necessarily represent the actual or relative thickness of each layer. The OLED device includes a substrate 100, an anode 102, a hole injection modification layer 110, a hole transporting layer 120, an electron blocking layer (not shown), a light-emitting layer 130, a hole blocking layer 140, an electron transporting layer 150, and a cathode 104. It is optional to include or not include an electron blocking layer and hole injection modification layer 110 in the device structure, as dictated by the desired characteristics of a particular device. The layers disposed between the anode and the cathode constitutes the electroluminescent medium 400 of the device. For example, as shown in FIG. 1, electroluminescent medium 400 comprises hole injection modification layer 110, hole transporting layer 120, optional electron blocking layer (not shown), light-emitting layer 130, hole blocking layer 140, and electron transporting layer 150. Light-emitting layer 130 comprises a host material in which at least one phosphorescent iridium complex of the present disclosure resides as a dopant. Substrate 100 may be made of glass, plastic or other appropriate materials. Anode 102 may be made of an electrically-conductive metal oxide such as indium tin oxide (ITO), a mixture of electrically-conductive metal oxides, or a laminate of one or more electrically-conductive metal oxides. In certain embodiments, the electrically-conductive metal oxide is ITO from the standpoint of producibility, electrical conductivity, and transparency. The material forming cathode 104 can be a metal, an alloy or mixture thereof. Examples of cathode materials include gold, silver, lead, aluminum, magnesium-silver alloys, and mixture thereof. Cathode 104 can be in the form of a single layer structure comprising one of the foregoing cathode materials, a mixture of the foregoing cathode materials, or can be in the form of a laminated structure in which each layer comprises one or more of the foregoing cathode materials.

A top emission device can be manufactured using the following method. A glass substrate is used for forming the device. An opaque and reflective anode, a hole injection modification layer (optional), a hole transporting layer, a light-emitting layer, a hole blocking layer, an electron transporting layer, and an election injection layer of potassium fluoride (optional), and a transparent cathode are sequentially formed on the substrate. The anode can be made of electrically conductive Al/Ni or Al/TiO with an overall thickness of about 100 nanometers. The light-emitting layer comprises a host material in which at least one phosphorescent iridium complex of the disclosure resides as a dopant. An opaque and reflective anode can be produced by sequentially depositing Al and Ni (or Al and TiO) on the glass substrate by thermal evaporation in high vacuum. Before the anode layer is further processed, the surface of the anode can be treated with oxygen plasma or UV—$O_3$. The cathode of a top emission device can be made of a low work function metal such as, for example, Ca or Mg, with an overall thickness of about 20 nanometers. An organic or inorganic material with high refractive index can be deposited on the cathode comprising a low work function metal as a protection layer. The protection layer can increase the amount of emitted light and thereby improve the emission efficiency and lifetime of the device. Examples of high refractive index materials suitable for forming a protection layer include inorganic materials such as ZnSe, ZnS, $TiO_2$, ITO, and organic materials such as aromatic amines (e.g., 2-TNATA and IDE320).

A hole injection modification layer of the present disclosure can comprise, for example, m-MTDATA (4,4',4"-tris [N-(3-methylphenyl)-N-phenylamino] triphenylamine), 2-TNATA (4,4',4"-tris [2-naphthylphenylamino] triphenylamine), CuPc (copper phthalocyanine) or IDE406 (commercially available from Idemitsu Kosen).

The structural formulae of group G1 compounds is shown below:

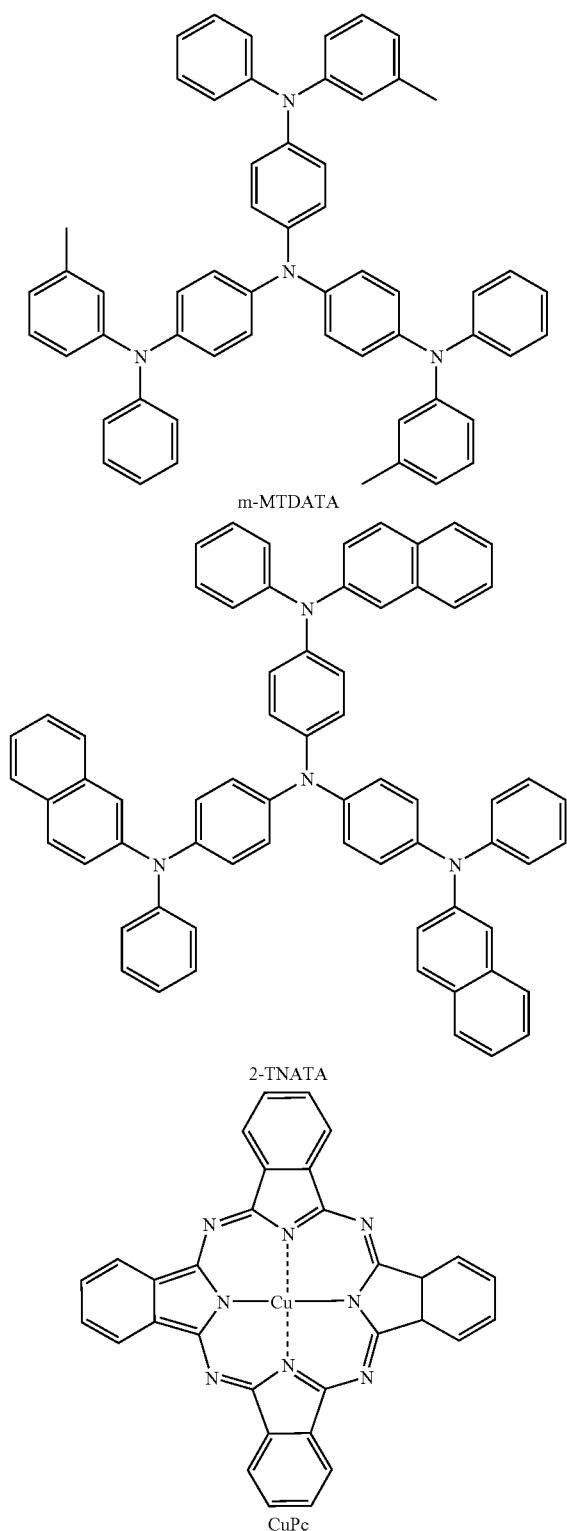

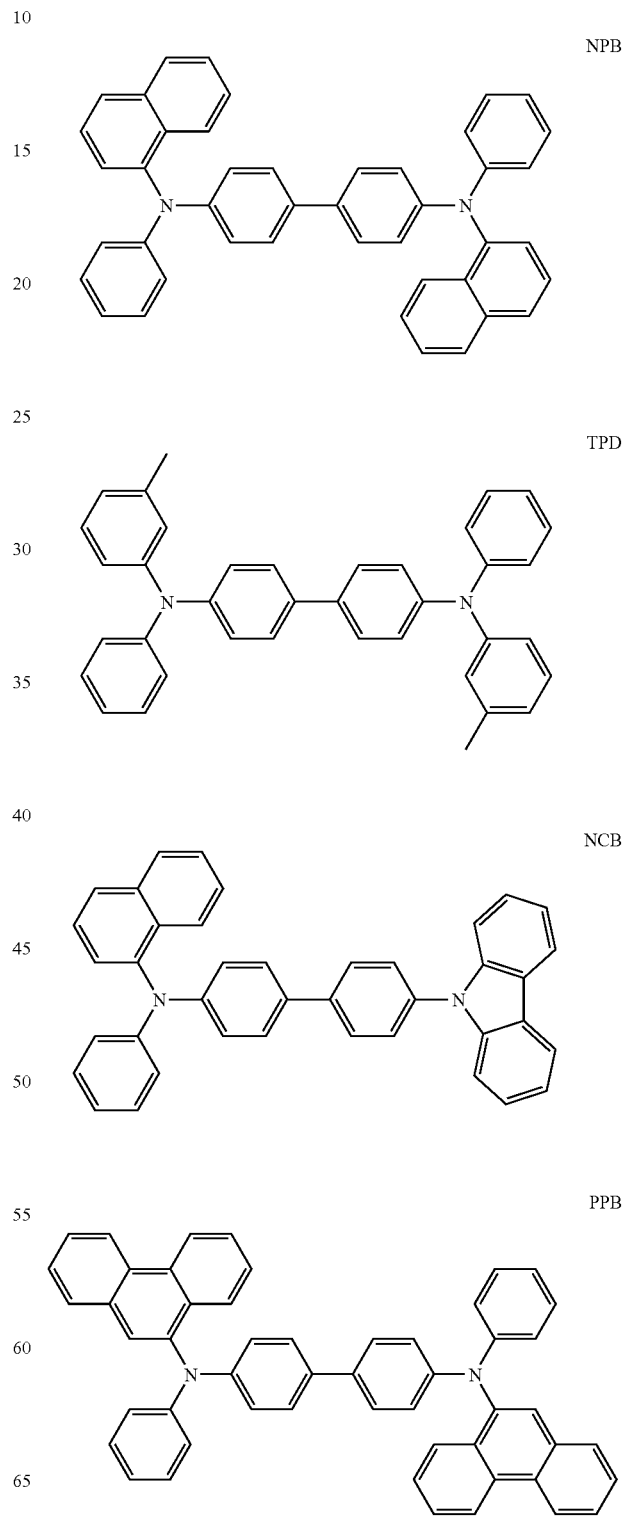

carbazolyl] triphenylamine), MPMP (bis{4-[N,N-diethylamino]-2-[methylphenyl]}-[4-methylphenyl]methane), HMTPD (4,4,-bis {N, N'-[3-tolyl]amino}-3,3'-dimethylbiphenyl) or IDE320 (commercially available from Idemitsu Kosen).

The structural formulae for group G2 compounds is shown below:

A hole transporting layer of the present disclosure can comprise, for example, NPB (4,4'-bis[1-naphthylphenylamino]biphenyl), TPD (4,4'-bis [m-tolylphenylamino]biphenyl), NCB (4-[N-carbazolyl]-4'-[N-phenylnaphthylamino] biphenyl), PPB (4,4'-bis [9-phenanthrylphenylamino]biphenyl), TCTA (4,4',4"-tri[N-

MPMP

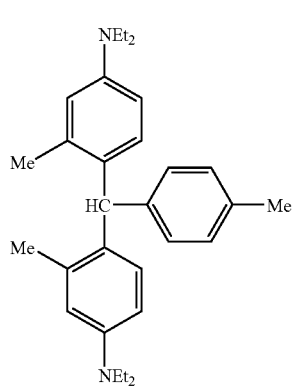

HMTPD

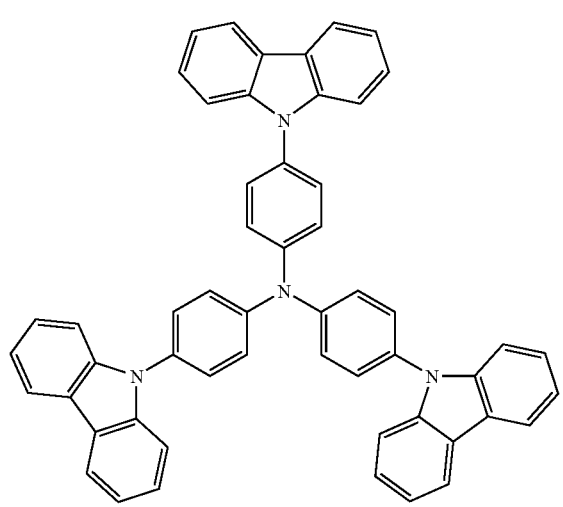

TCTA benzene), and CDBP (4,4'-bis[9-carbazolyl]-2,2'-dimethyl-biphenyl) which has the Formula shown in the structural Formula group G3), and electron-transporting materials (e.g., TPBI (1,3,5-tris [N-phenylbenzimidazol-2-yl]benzene), TAZ-1 (3-phenyl-4-[1'-naphthyl]-5-phenyl-1,2,4-triazole), TAZ-2 (3-[4-biphenylyl]-4-phenyl-5-tert-butylphenyl-1,2,4-triazole), TAZ-3 (3-phenyl-4-[1'-phenyl]-5-phenyl-1,2,4-triazole), PBD (2-[4-biphenyl]-5-[4-tert-butylphenyl]-1,3,4-oxadiazole), and TMM004 (commercially available from Covion) which has the Formula shown in group G4).

The structural formulae of group G3 compounds is shown below:

mCP

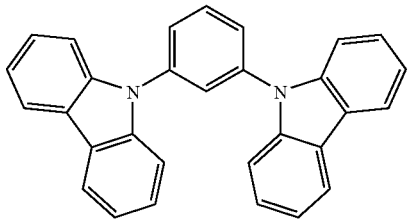

TCB

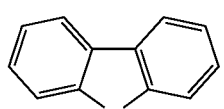

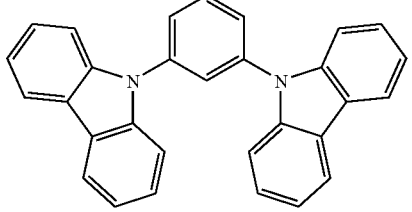

TCPB

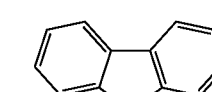

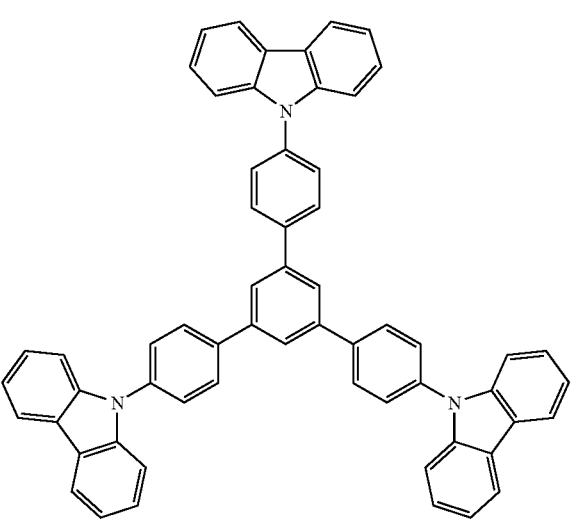

Examples of host materials include TCTA shown in group G2, hole-transporting materials (e.g., CBP (4,4'-N,N'-dicarbazole-biphenyl), CCP (1,4-bis [carbazolyl]benzene), TCPB (1,3,5-tris [4-(N-carbazolyl)phenyl]benzene), mCP (N, N'-dicarbazolyl-3,5-benzene), TCB (1,3,5-tris[carbazolyl]

-continued

CBP

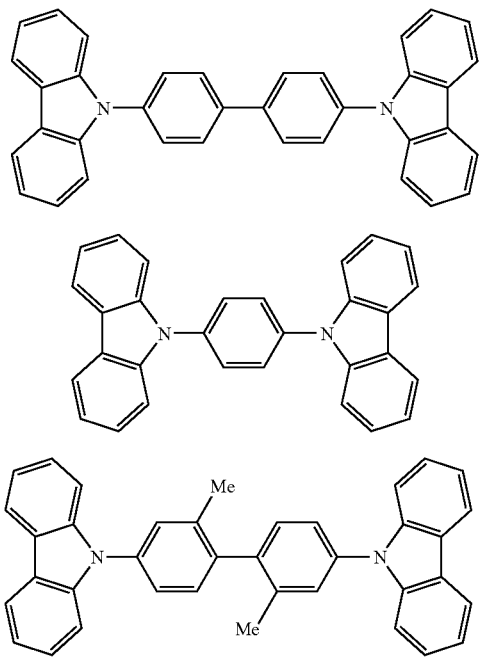

CCP

CDBP

The structural formulae of group G4 compounds is shown below:

TPBI

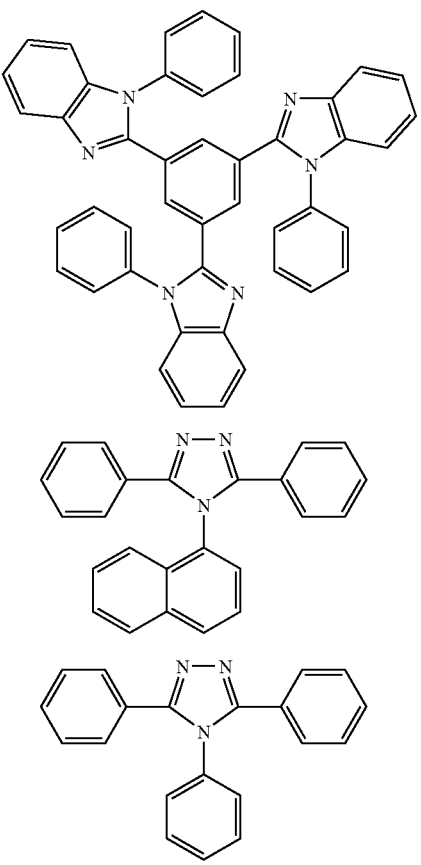

TAZ-1

TAZ-3

-continued

TAZ-2

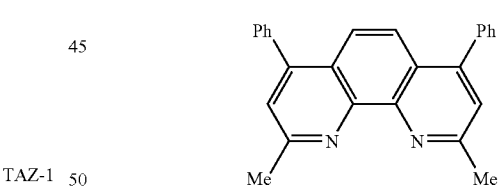

PBD

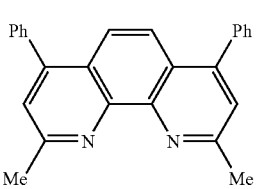

A hole blocking modification layer of the present disclosure can comprise, for example, TPBI as shown in group G4, BCP (2,9-dimethyl-4,7-diphenyl-1,10-phenanthroline), BAlq (aluminum[III]bis[2-methyl-8-quinolinato][4-phenylphenolate]), PAlq (aluminum[III]bis[2-methyl-8-quinolinato]-[4-phenolate]), or SAlq (aluminum[III]bis[2-methyl-8-quinolinato][triphenylsilanolate]) which has the Formula shown in group G5. Examples of electron-transporting materials include TPBI, TAZ-1, TAZ-2, TAZ-3, PBD shown in group G4, Alq$_3$ (tris[8-hydroxyquinolinato]aluminum), DPA (4,7-diphenyl-1,10-phenanthroline) which has the Formula shown in group G5, and TYE704 (commercially available from Toyo Ink).

The structural formulae of group G5 compounds is shown below:

BCP

PAlq

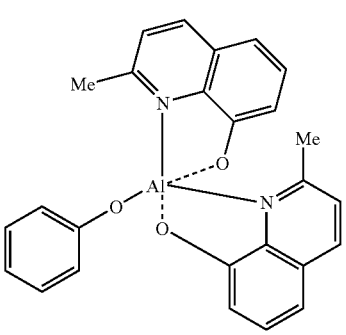

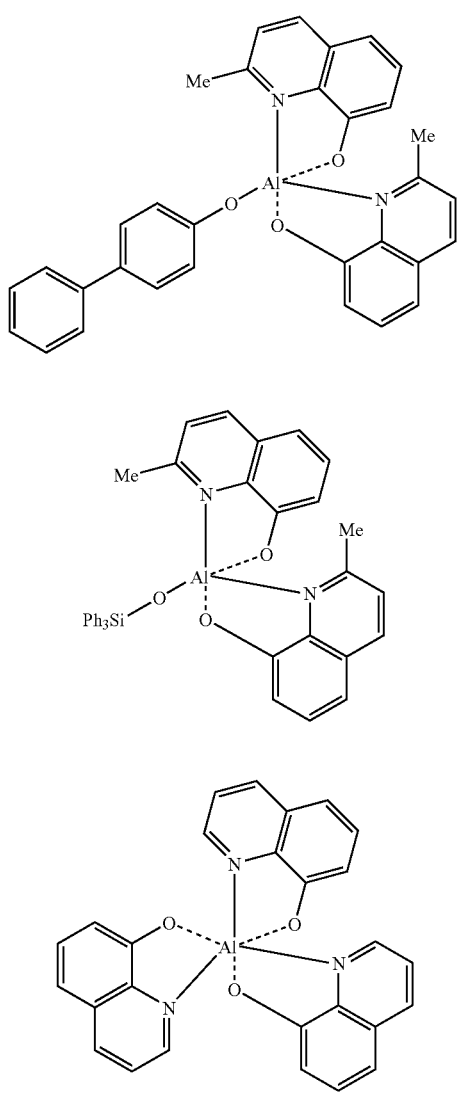

BAlq

SAlq

Alq3

DPA

In groups G3–G5, Ph represents a phenyl group, Me represents a methyl group, Et represents an ethyl group, and Bu represents a butyl group.

EXAMPLES

Embodiments of the present disclosure can be further defined by reference to the following examples, which describe in detail preparation of iridium compounds and light-emitting elements of the present disclosure and procedures for characterizing iridium compounds and light-emitting elements of the present disclosure. It will be apparent to those skilled in the art that many modifications, both to materials and methods, may be practiced without departing from the scope of the present disclosure.

In the examples below, the following abbreviations have the following meanings. If an abbreviation is not defined, it has its generally accepted meaning.

cd/A=current efficiency, candela per Amp
$cd/m^2$=brightness, luminance efficiency, candela per square meter
g=gram
mL=milliliter
min=minute
mm=millimeter
nm=nanometer
ITO=indium tin oxide
h=hour
mol=mole
mmole=millimole
nm=nanometer
PL=photoluminescence
UV=ultraviolet
V=volt Example 1

Synthesis of Mpb

The synthesis of 1-methyl-2-phenyl-1H-benzoimidazole (Mpb) is accomplished by referring to methods disclosed in Popov, I. I., Chem. Heterocycl. Compd. (EN), 1996, 32, 6, p. 672–681. The synthetic method is outlined in Scheme 1. To 20 mL acetone was added 2-phenyl-1H-benzoimidazole (1.94 g, 10 mmol), followed by the injection of iodomethane (1.42 mL, 12 mmol). The mixture was stirred at room temperature for 6 h, sodium hydroxide solution was then added, and the mixture reacted for an additional 5 min. The reaction mixture was extracted with dichloromethane. The organic layer was dried over magnesium sulfate and concentrated under reduced pressure. The residue was purified by column chromatography using n-hexanes/EA (v/v=80/20) as eluent. After the product was completely isolated, 1.03 mg (0.49 mmol) of the title compound was obtained (49% yield). $^1$H NMR (CDCl$_3$, δ): 3.87 (s, 3 H), 7.32–7.41 (m, 3 H), 7.51–7.56 (m, 3 H), 7.83–7.86 (m, 3 H).

Scheme 1

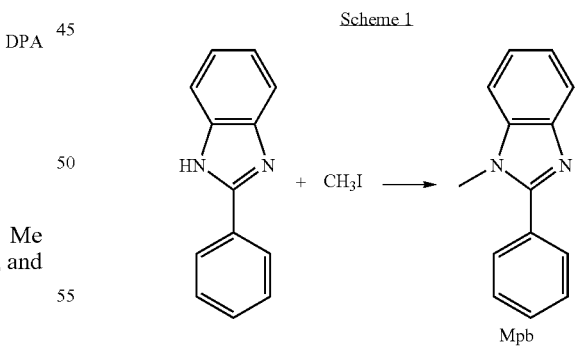

Example 2

Synthesis of Epb

The synthesis of 1-ethyl-2-phenyl-1H-benzoimidazole (Epb) was accomplished according to the methods disclosed in Huebner, Chem. Ber. 1876, 9, p. 776. The synthetic methods are outlined in Scheme 2 and the detailed steps are similar to those described in Example 1 except that iodomethane was replaced by iodoethane. The desired product was obtained in 42% yield. $^1$H NMR (CDCl$_3$, δ): 1.46 (t, J=7.6 Hz, 3 H), 4.26 (q, J=14.4 Hz, J=7.6 Hz, 2 H), 7.42–7.48 (m, 3 H), 7.50–7.56 (m, 3 H), 7.71–7.81 (m, 3 H).

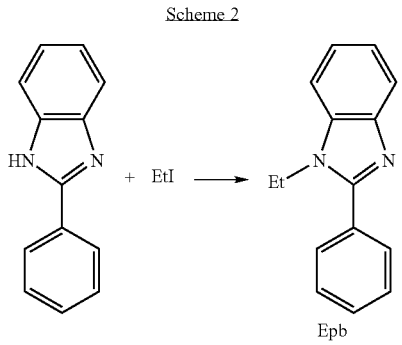

Scheme 2

Example 3

Synthesis of Dpb

The synthesis of 1,2-diphenyl-1H-benzoimidazole (Dpb) is outlined in Scheme 3. To a round round-bottom flask (50 mL) was added N-phenyl-1,2-phenylene diamine (10 mmol) and benzaldehyde (20 mmol) which was allowed to react in a Kugelrohr oven at 110° C. for one hour. After the unreacted benzaldehyde was removed under vacuum, the crude product of high purity was obtained by raising the temperature to 180° C. Recrystallization of the crude product from Hexane/CH$_2$Cl$_2$ gave a white crystal of the title compound in 55% yield.

Scheme 3

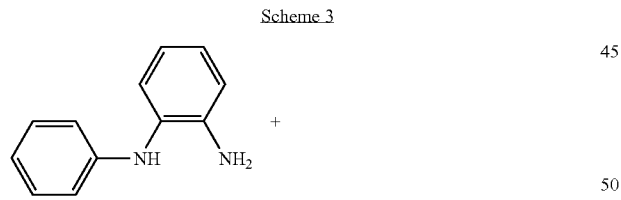

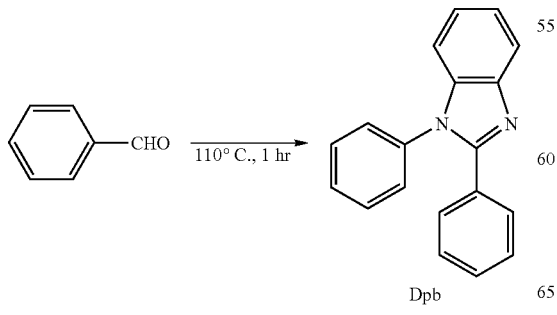

Example 4

Synthesis of Bpb

The synthetic sequences of 1-benzyl-2-phenyl-1H-benzoimidazole (Bpb) are outlined in Scheme 4. 1,2-phenylenediamine (1.08 g, 10 mmol) and ethanol (20 mL) was added to a flask. The reaction mixture was allowed to stir for a few minutes, and then benzaldehyde (2.16 g, 20.4 mmol) was added. The resulting solution was then heated and allowed to reflux for 6 h. The reaction mixture was then cooled, precipitated, and filtered. The solid product was recrystallized from hexanes/CH$_2$Cl$_2$ to obtain 2.08 g of the title compound in 73% yield.

Scheme 4

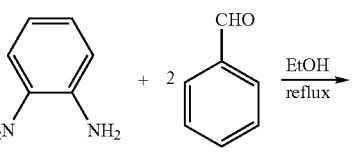

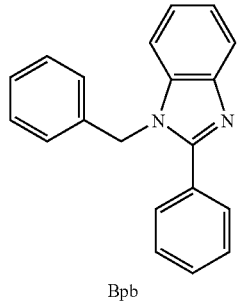

Example 5

Synthesis of Dfbpb

The synthesis of 1-[2,4-difluoro-benzyl]-2-[2,4-difluoro-phenyl]-1H-benzoimidazole (Dfbpb) is outlined in Scheme 5. To anhydrous ethanol (20 mL) was added 2,4-difluorobenzaldehyde (2.89 g, 20.4 mmol) and then added 1,2-phenyldiamine (1.08 g, 10 mmol). The reaction mixture was then heated and allowed to reflux for 6 h. The reaction mixture was then cooled, precipitated, and filtered. The solid product was recrystallized twice from 95% alcohol to obtain 2.83 g of final product in 79% yield.

Scheme 5

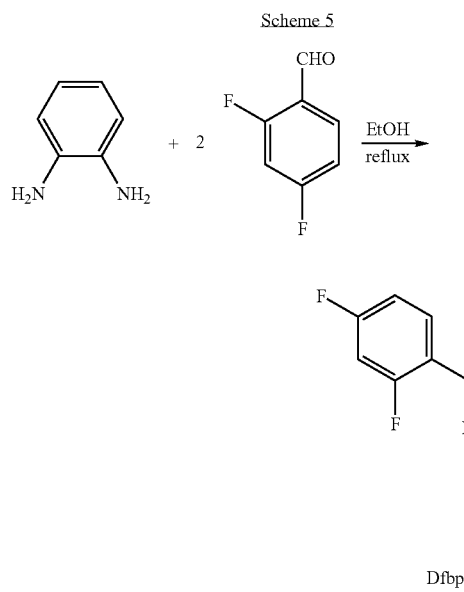

Dfbpb

Example 6

Synthesis of MObpb

The synthesis of 1-[4-methoxy-benzyl]-2-[4-methoxy-phenyl]-1H-benzoimidazole (MObpb) is outlined in Scheme 6. Similar to the detailed steps described in Example 4 and Example 5, to anhydrous ethanol was added 4-methoxybenzaldehyde (2.77 g, 20.4 mmol) and then added 1,2-phenyldiamine (1.08 g, 10 mmol). The reaction mixture was then heated and allowed to reflux for 6 h. The reaction mixture was then cooled, precipitated, and filtered. The solid product was recrystallized twice from 95% alcohol to obtain 2.97 g of the title compound in 86% yield.

Scheme 6

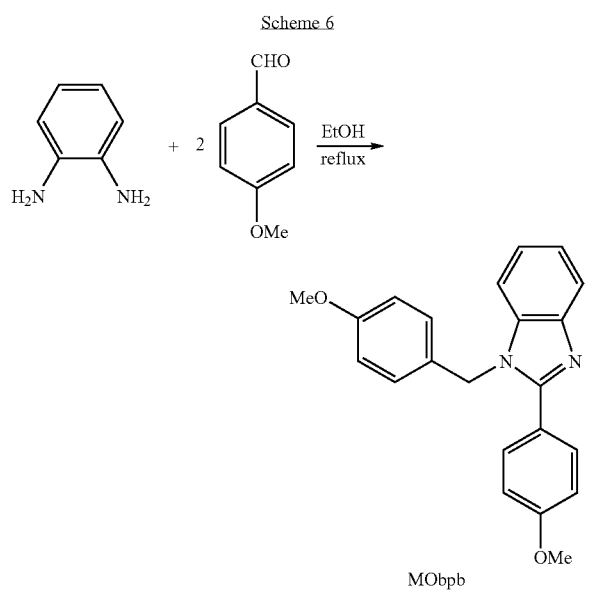

MObpb

Example 7

Synthesis of Mbpb

The synthesis of 1-[4-methyl-benzyl]-2-[4-methyl-phenyl]-1H-benzoimidazole (Mbpb) is outlined in Scheme 7 and the detailed steps are similar to those described in Example 6.

Scheme 7

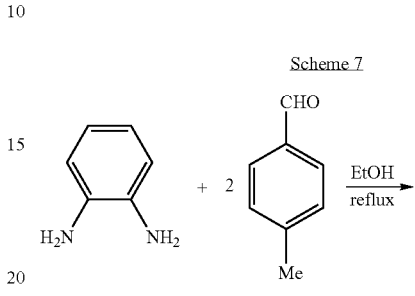

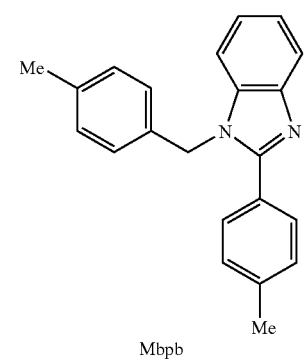

Mbpb

Example 8

Synthesis of Tbtpb

The synthesis of 1-[2-trifluoromethyl-benzyl]-2-[2-trifluoromethyl-phenyl]-1H-benzoimidazole (Tbtpb) is outlined in Scheme 8. Similar to the detailed steps described in Example 4 and Example 5, to anhydrous ethanol was added 2-[trifluoromethyl]benzaldehyde (3.55 g, 20.4 mmol) and then added 1,2-phenyldiamine (1.08 g, 10 mmol). The reaction mixture was then heated and allowed to reflux for 6 h. The reaction mixture was then cooled, precipitated, and filtered. The solid product was recrystallized twice from 95% alcohol to obtain 3.57 g of the title compound in 85% yield.

Scheme 8

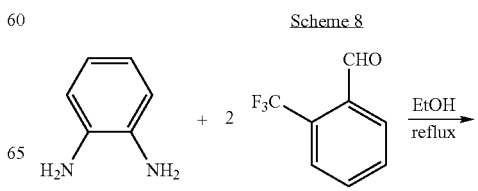

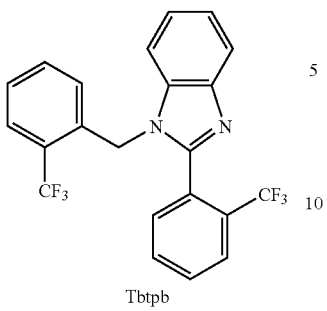

Tbtpb

Example 9

Synthesis of Dfppb

The synthesis of 2-[2,4-difluoro-phenyl]-1-phenyl-1H-benzoimidazole (Dfppb) is outlined in Scheme 9 and the detailed steps are similar to those described in Example 3 except that benzaldehyde was replaced by 2,4-difluoro-benzaldehyde. Recrystallization of the crude product from Hexane/$CH_2Cl_2$ gave a white crystal of the title compound in 55% yield.

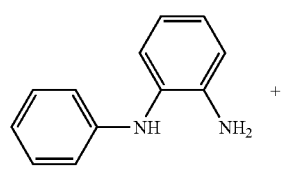

Scheme 9

Example 10

Synthesis of Fppb

The synthesis of 2-[4-fluoro-phenyl]-1-phenyl-1H-benzoimidazole (Fppb) is outlined in Scheme 10 and the detailed steps are similar to those described in Example 3 except that benzaldehyde was replaced by 4-fluoro-benzaldehyde. Recrystallization of the crudeproduct from Hexane/$CH_2Cl_2$ gave a white crystal of the title compound in 60% yield.

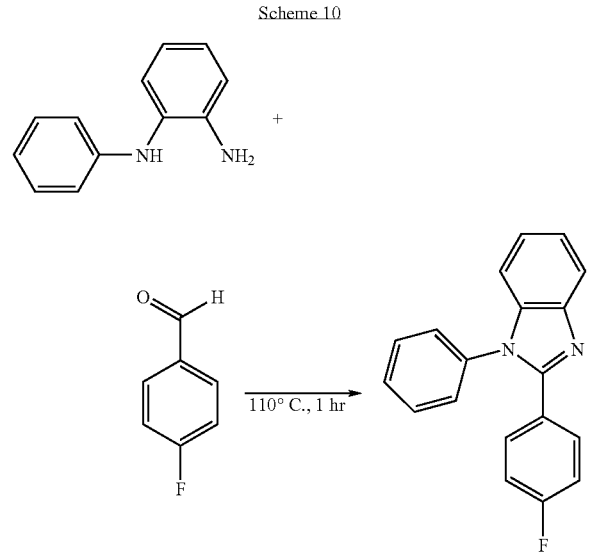

Scheme 10

Fppb

Example 11

Synthesis of Ptpb

The synthesis of 1-Phenyl-2-(4-trifluoromethyl-phenyl)-1H-benzoimidazole (Ptpb) is outlined in Scheme 11 and the detailed steps are similar to those described in Example 3 except that benzaldehyde was replaced by 4-trifluoromethyl-benzaldehyde. Recrystallization of the crude product from Hexane/$CH_2Cl_2$ gave a white crystal in 58% yield.

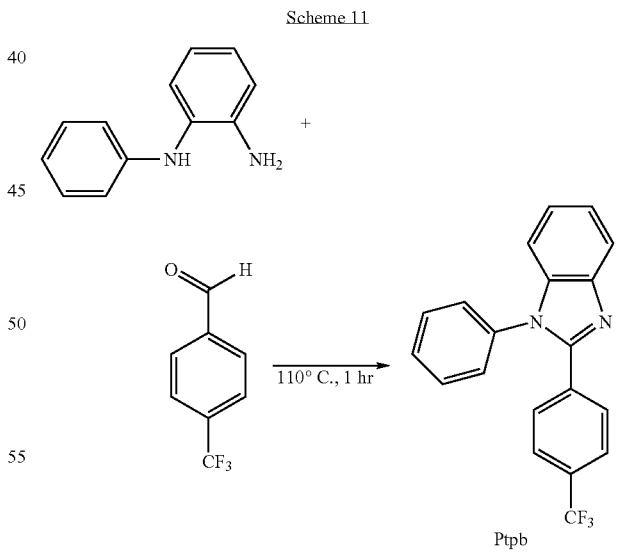

Scheme 11

Ptpb

Example 12

Synthesis of Bdmpb

The synthesis of 1-benzyl-5,6-dimethyl-2-phenyl-1H-benzoimidazole (Bdmpb) is outlined in Scheme 12. Similar to the detailed steps described in Example 4 and Example 5, to ethanol (20 mL) was added benzaldehyde (2.16 g, 20.4 mmol) and then added 4,5-dimethyl-benzene-1,2-diamine (1.36 g, 10 mmol). The reaction mixture was then heated and allowed to reflux for 6 h. The reaction mixture was then cooled to room temperature, precipitated, and filtered. The solid product was recrystallized twice from 95% alcohol to obtain 2.43 g of the title compound in 77% yield. $^1$H NMR (CDCl$_3$, δ): 2.31 (s, 3 H), 2.37 (s, 3 H), 5.39 (s, 2 H), 6.96 (s, 1 H), 7.08 (d, J=6.8 Hz, 2 H), 7.28–7.33 (m, 3 H), 7.40–7.58 (m, 3 H), 7.62–7.65 (m, 3 H).

Scheme 12

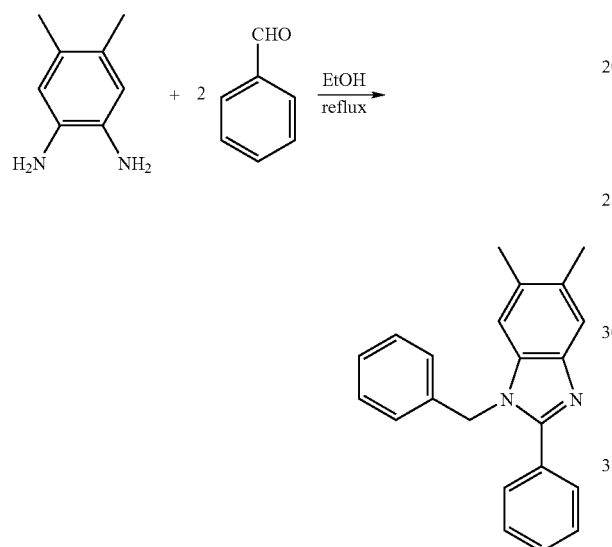

Bdmpb

Example 13

Synthesis of Iridium Complex (L)$_2$Ir(acac)

The synthesis of (L)$_2$Ir(acac) is outlined in Scheme 13. To 2-ethoxyethanol (10 mL) was added 1 mmol of one of the compounds obtained in Examples 1, 2, or 4–9, and then added 1 mmol of iridium trichloride hydrate and water (3 mL). The reaction mixture was then stirred under nitrogen gas at 80° C. for 12 h. The mixture was cooled to room temperature and filtered. The collected solid was washed with ethanol and n-hexane several times, and dried under vacuum to produce cyclometalated Ir(III)-μ-chloro-bridged dimer. The iridium chloro-bridged dimer, acetylacetone (5 mmol), and Na$_2$CO$_3$ (10 mmol) was dissolved in 2-ethoxyethanol (15 mL) and the reaction mixture stirred under nitrogen at 80° C. for 6 h. The mixture was cooled to room temperature and filtered. The collected solid was sequentially washed with water, ethanol, and ether, and purified by vacuum sublimation to give the title compound.

Scheme 13

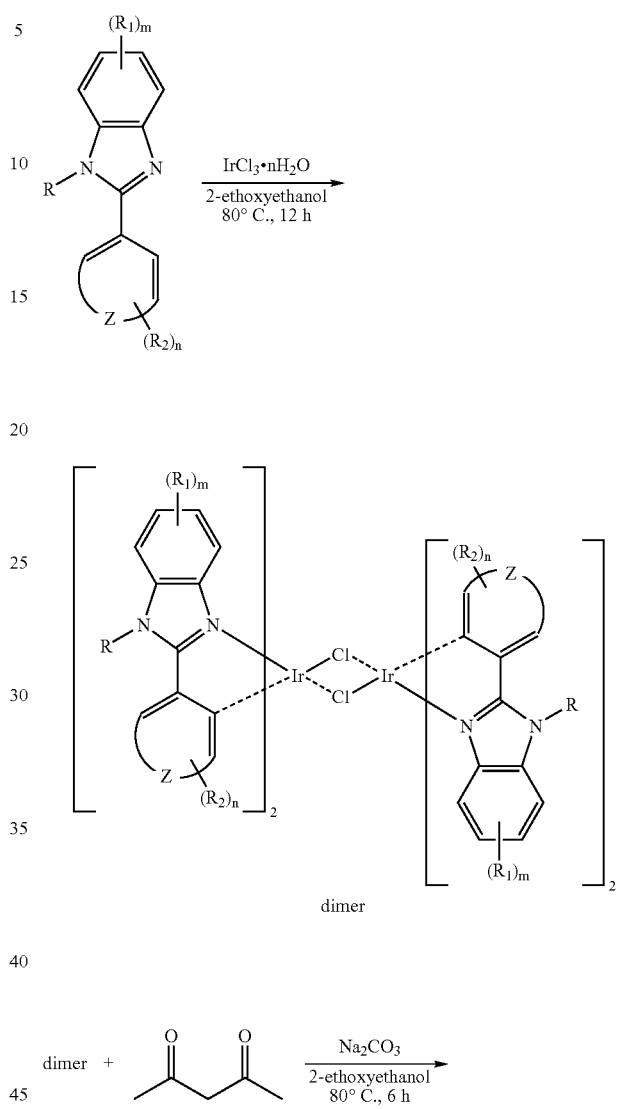

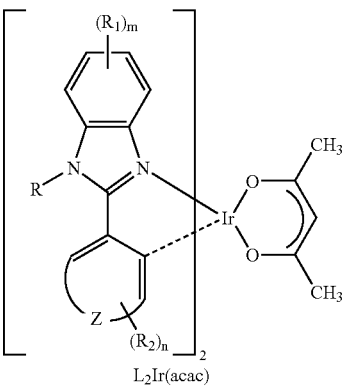

L$_2$Ir(acac)

Example 14

Synthesis of Ir(Mpb)$_2$(acac) (II-1)

Figure 2:
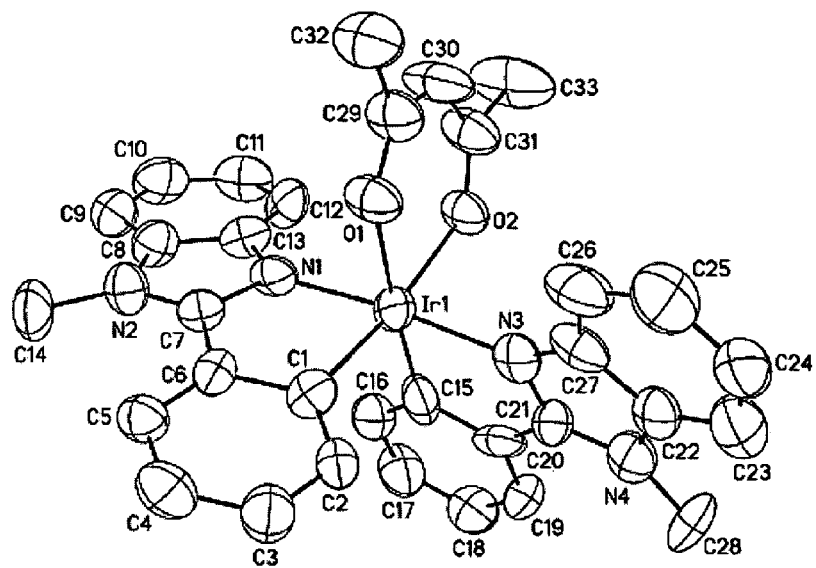
FIG. 2 represents the X-ray structure of the complex II-1.
Figure 3:
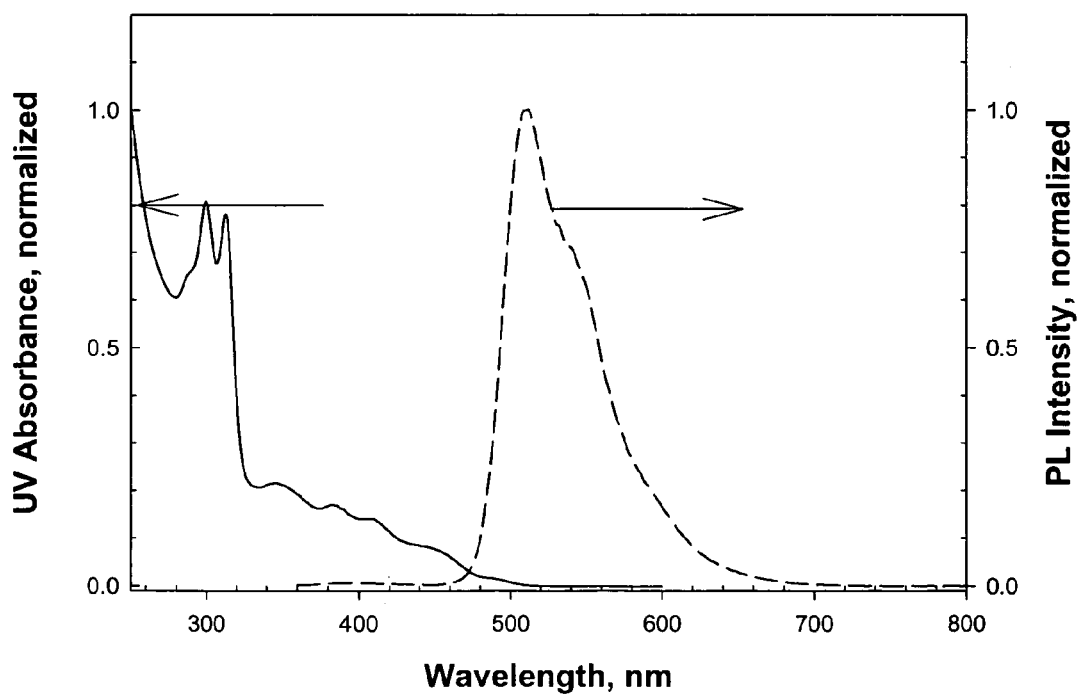
FIG. 3 represents the UV absorption spectrum (represented by the solid line, left y-axis) and the phosphorescence emission spectrum (represented by the dotted line, right y-axis) of the complex II-1 dissolved in dichloromethane.

Mpb obtained in Example 1 was used as the ligand (L) to produce the title complex II-1 in a yield of 76% according to the detailed steps described in Example 13. The X-ray structure of complex II-1 is shown in FIG. 2. The UV absorption spectrum and the phosphorescence emission spectrum of complex II-1 in dichloromethane are shown in FIG. 3. The complex II-1 emits a green light having a peak wavelength of 510 nm. $^1$H NMR (CDCl$_3$, δ): 1.76 (s, 6 H), 4.25 (s, 6 H), 5.15 (s, 1 H), 6.38 (d, J=7.6 Hz, 2 H), 6.57 (t, J=8.0 Hz, 2 H), 6.78 (t, J=7.6 Hz, 2 H), 7.26 (t, J=8.4 Hz, 2 H), 7.37 (t, J=7.2 Hz, 2 H), 7.44 (d, J=8.4 Hz, 2 H), 7.65 (d, J=8.0 Hz, 2 H), 7.75 (d, J=8.4 Hz, 2 H). HRMS (EI): calculated for C$_{33}$H$_{29}$IrO$_2$N$_4$ (M$^+$) 706.1920, measured 706.1926.

Example 15

Synthesis of Ir(Epb)$_2$(acac) (II-2)

Figure 4:
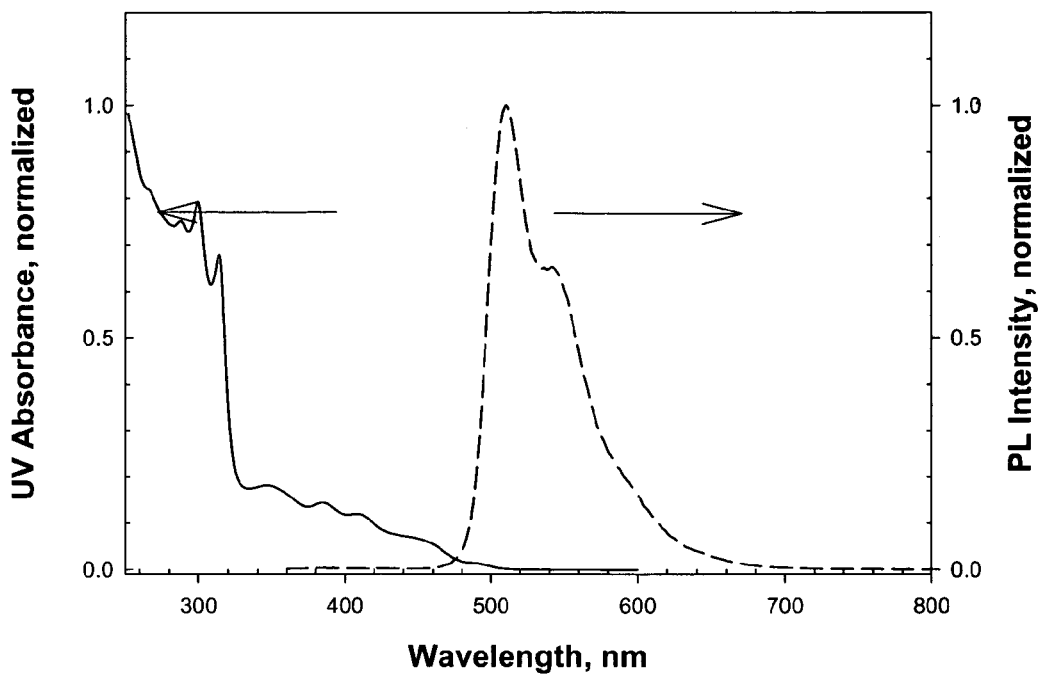
FIG. 4 represents the UV absorption spectrum (represented by the solid line, left y-axis) and the phosphorescence emission spectrum (represented by the dotted line, right y-axis) of the complex II-2 dissolved in dichloromethane.

Epb obtained in Example 2 was used as the ligand (L) to produce the title complex II-2 in a yield of 71 % according to the detailed steps described in Example 13. The UV absorption spectrum and the phosphorescence emission spectrum of complex II-2 in dichloromethane are shown in FIG. 4. The complex II-2 emits a green light having a peak wavelength of 510 nm. $^1$H NMR (CDCl$_3$, δ): 1.64 (t, J=7.32 Hz, 6 H), 1.73 (s, 6 H), 4.74 (m, 4 H), 5.15 (s, 1 H), 6.35 (d, J=7.6 Hz, 2 H), 6.55 (t, J=7.2 Hz, 2 H), 6.78 (t, J=7.6 Hz, 2 H), 7.25 (t, J=8.0 Hz, 2 H), 7.33 (t, J=8.0 Hz, 2 H), 7.44 (d, J=7.6 Hz, 2 H), 7.58 (d, J=7.6 Hz, 2 H), 7.65 (d, J=8.0 Hz, 2 H). HRMS (EI): calculated for C$_{35}$H$_{33}$IrN$_4$O$_2$ (M$^+$) 734.2233, measured 734.2229.

Example 16

Synthesis of Ir(Dpb)$_2$(acac) (II-3)

To a flask with side neck (25ml) was added 1 mmol of iridium trichloride hydrate, 2.5 mmol of Dpb obtained in Example 3, and 10 mL of 2-ethoxyethanol/water (3/1). The reaction mixture was allowed to react at 80° C. for 6 h. After filtering the yellow precipitate, the residual liquid was added back to the flask and allowed to react for another 6 h. The yellow precipitate was filtered again and washed with a small amount of ethanol and n-hexane. The precipitate was scraped, dried, and weighed to give a yellow iridium dimer in 90% yield.

Figure 5:
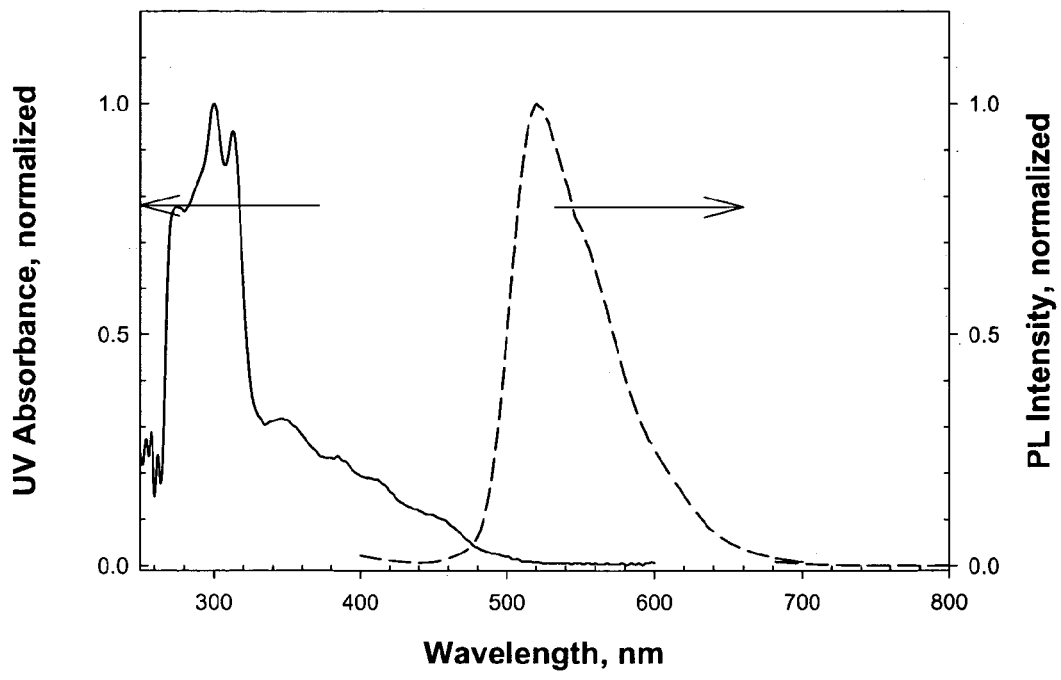
FIG. 5 represents the UV absorption spectrum (represented by the solid line, left y-axis) and the phosphorescence emission spectrum (represented by the dotted line, right y-axis) of the complex II-3 dissolved in dichloromethane.

To a flask with side neck (25 mL) was added 1 mmol of the yellow iridium dimer product, acetylacetone (2 mmol), Na$_2$CO3 (10 mmol), and 2-ethoxyethanol (4 mL). The reaction mixture was allowed to react at 50° C. for 3 h and then distilled under reduced pressure to remove the 2-ethoxyethanol. The residue was purified by column chromatography using n-hexane/EA (4/1) as eluent. The title iridium complex II-3 was obtained in 86% yield. The UV absorption spectrum and the phosphorescence emission spectrum of the complex II-3 in dichloromethane are shown in FIG. 5. The complex II-3 emits a green light having a peak wavelength of 518 nm. $^1$H NMR (CDCl$_3$, δ): 1.86 (s, 6 H), 5.27 (s, 1 H), 6.58–6.44 (m, 8 H), 7.32–7.26 (m, 4 H), 7.66–7.57 (m, 12 H), 7.77–7.72 (m, 2 H). $^{13}$C NMR (CDCl$_3$, δ): 28.45, 101.29, 110.30, 116.65, 119.81, 122.82, 123.89, 124.91, 128.29, 128.41, 128.87, 129.85, 130.21, 134.90, 135.13, 135.77, 136.52, 140.53, 149.76, 164.20, 184.80. HRMS (FAB): calculated for C$_{43}$H$_{33}$IrN$_4$O$_2$ (M$^+$) 830.2233, measured 830.2247.

Example 17

Synthesis of Ir(Bpb)$_2$(acac) (II-4)

Figure 6:
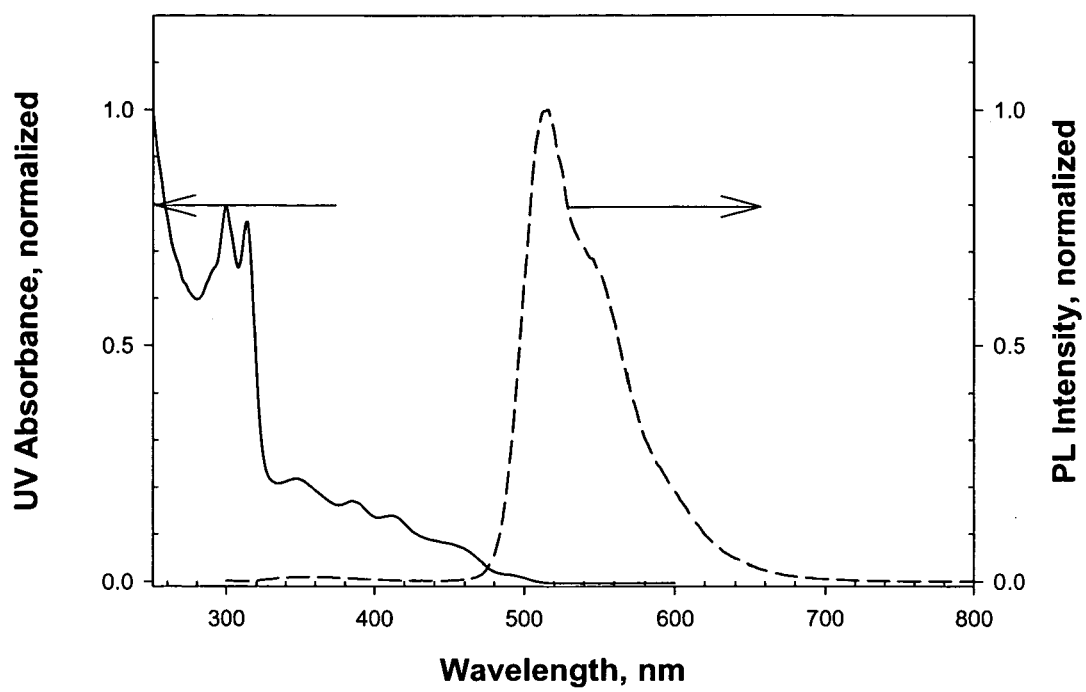
FIG. 6 represents the UV absorption spectrum (represented by the solid line, left y-axis) and the phosphorescence emission spectrum (represented by the dotted line, right y-axis) of the complex II-4 dissolved in dichloromethane.

Bpb obtained in Example 4 was used as the ligand (L) to produce the title complex II-4 in a yield of 75% according to the detailed steps described in Example 13. The UV absorption spectrum and the phosphorescence emission spectrum of complex II-4 in dichloromethane are shown in FIG. 6. The complex II-4 emits a green light having a peak wavelength of 516 nm. $^1$H NMR (CDCl$_3$, δ): 1.84 (s, 6 H), 5.30 (s, 1 H), 5.96 (dd, J=16.0 Hz, J=12.4 Hz, 4 H), 6.40 (d, J=7.6 Hz, 2 H), 6.58 (t, J=7.2 Hz, 2 H), 6.73 (t, J=8.0 Hz, 2 H), 7.22 (d, J=6.8 Hz, 4 H), 7.29–7.32(m, 10 H), 7.34 (d, J=6.0 Hz, 2 H), 7.36 (d, J=6.4 Hz, 2 H), 7.67 (d, J=8.0 Hz, 2 H). HRMS (FAB): calculated for C$_{45}$H$_{37}$IrN$_4$O$_2$ (M$^+$) 858.2546, measured 858.2540.

Example 18

Synthesis of Ir(Dfbpb)$_2$(acac) (II-5)

Figure 7:
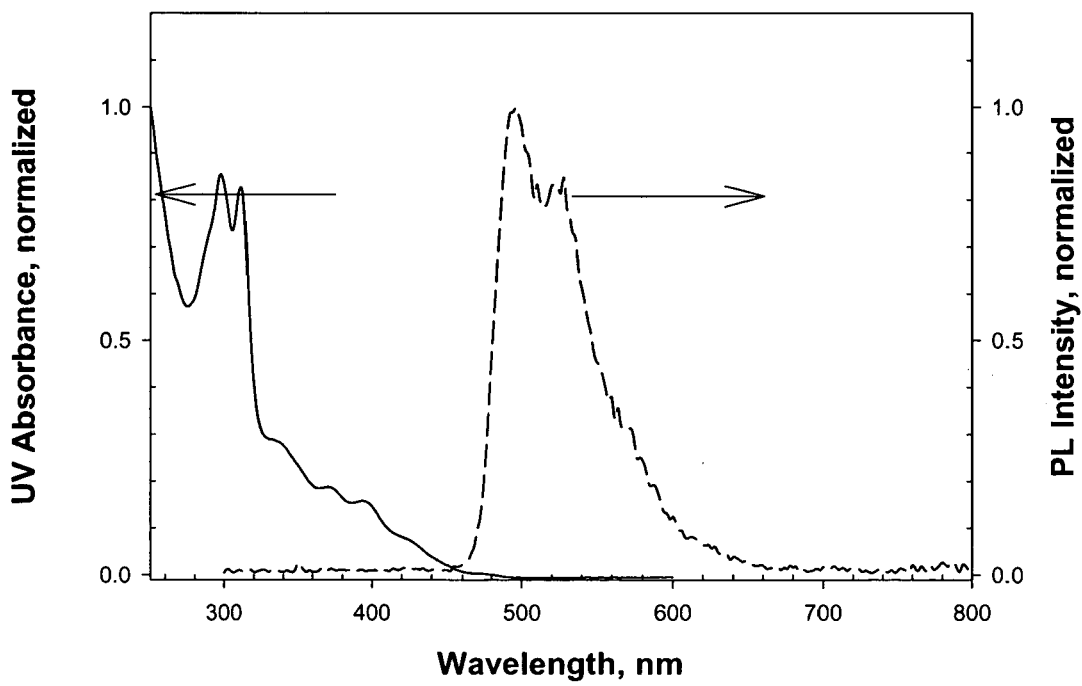
FIG. 7 represents the UV absorption spectrum (represented by the solid line, left y-axis) and the phosphorescence emission spectrum (represented by the dotted line, right y-axis) of the complex II-5 dissolved in dichloromethane.

Dfbpb obtained in Example 5 was used as the ligand (L) to produce the title complex II-5 according to the detailed steps described in Example 13. The UV absorption spectrum and the phosphorescence emission spectrum of the complex II-5 in dichloromethane are shown in FIG. 7. The complex II-5 emits a blue-green light having a peak wavelength of 496 nm. HRMS (FAB): calculated for C$_{45}$H$_{29}$F$_8$IrN$_4$O$_2$ (M$^+$) 1002.1792, measured 1002.1805.

Example 19

Synthesis of Ir(MObpb)$_2$(acac) (II-6)

Figure 8:
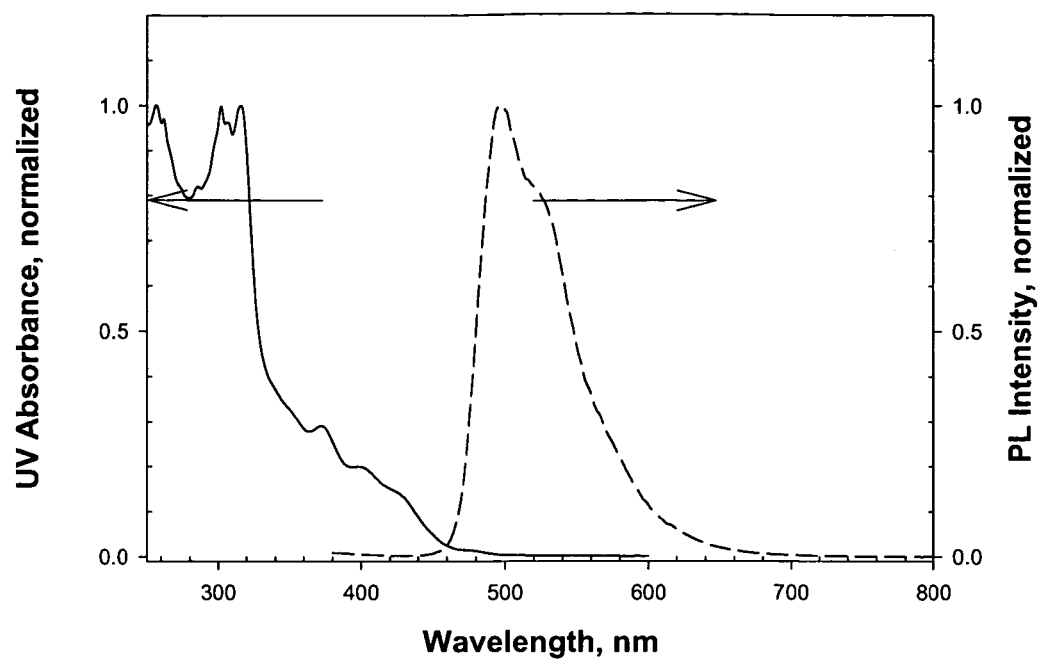
FIG. 8 represents the UV absorption spectrum (represented by the solid line, left y-axis) and the phosphorescence emission spectrum (represented by the dotted line, right y-axis) of the complex II-6 dissolved in dichloromethane.

MObpb obtained in Example 6 was used as the ligand (L) to produce the title complex II-6 in a yield of 83% according to the detailed steps described in Example 13. The UV absorption spectrum and the phosphorescence emission spectrum of the complex II-6 in dichloromethane are shown in FIG. 8. The complex II-6 emits a blue-green light having a wavelength of 496 nm. $^1$H NMR (CDCl$_3$, δ): 1.79 (s, 6 H), 3.27 (s, 6 H), 3.73 (s, 6 H), 5.21 (s, 1 H), 5.62 (d, J=16.8 Hz, 2 H), 5.79 (d, J=16.8 Hz, 2 H), 5.94 (d, J=2.4 Hz, 2 H), 6.16 (d, J=8.0 Hz, 2 H), 6.80 (d, J=8.8 Hz, 4 H), 7.11 (d, J=8.8 Hz, 4 H), 7.19–7.29 (m, 8 H), 7.66–7.69 (m, 2 H). HRMS (FAB): calculated for C$_{49}$H$_{45}$IrN$_4$O$_6$ (M$^+$) 978.2968, measured 978.2955.

Example 20

Synthesis of Ir(Mbpb)$_2$(acac) (II-7)

Figure 9:
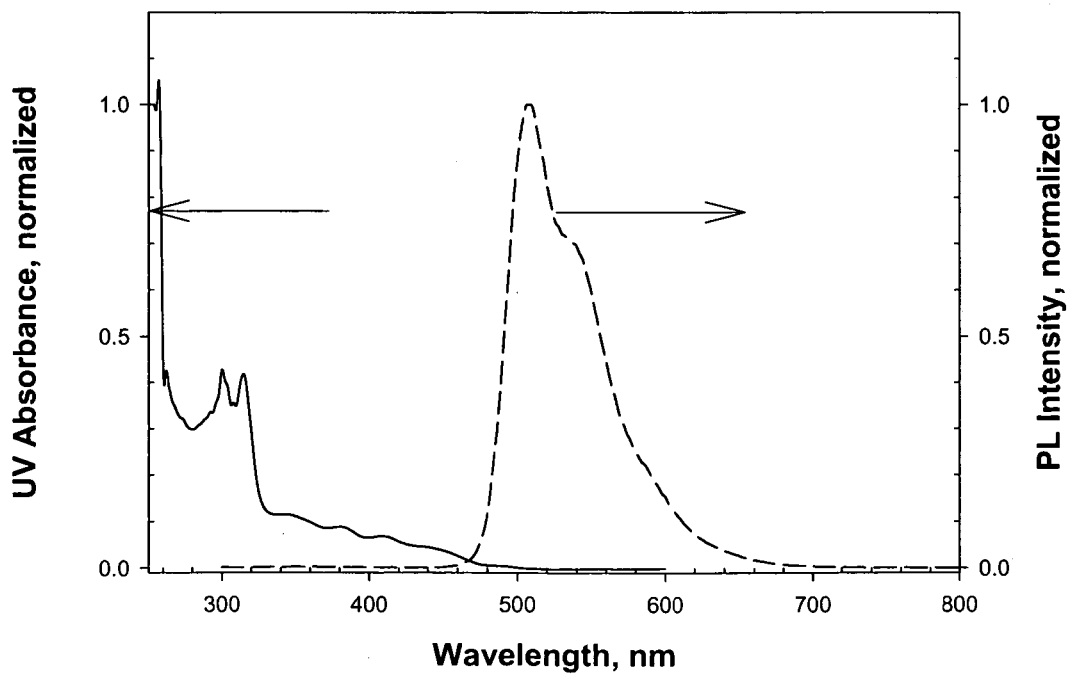
FIG. 9 represents the UV absorption spectrum (represented by the solid line, left y-axis) and the phosphorescence emission spectrum (represented by the dotted line, right y-axis) of the complex II-7 dissolved in dichloromethane.

Mbpb obtained in Example 7 was used as the ligand (L) to produce the title complex II-7 in a yield of 80% according to the detailed steps described in Example 13. The UV absorption spectrum and the phosphorescence emission spectrum of the complex II-7 in dichloromethane are shown in FIG. 9. The complex II-7 emits a green light having a peak wavelength of 508 nm. $^1$H NMR (CDCl$_3$, δ): 1.87 (s, 6 H), 1.94 (s, 6 H), 2.28 (s, 6 H), 5.35 (s, 1 H), 5.67 (d, J=16.8 Hz, 2 H), 5.89 (d, J=16.8 Hz, 2 H), 6.21 (d, J=2.4 Hz, 2 H), 6.67 (d, J=8.0 Hz, 2 H), 7.05–7.20 (m, 8 H), 7.35–7.50 (m, 8 H), 7.72 (m, 2 H). HRMS (FAB): calculated for $C_{49}H_{45}IrN_4O_2$ (M$^+$) 914.3172, measured 914.3181.

Example 21

Synthesis of Ir(Tbtpb)$_2$(acac) (II-8)

Tbtpb obtained in Example 8 was used as the ligand (L) to produce the title complex II-8 according to the detailed steps described in Example 13.

Example 22

Synthesis of Ir(Phb)$_2$(acac) (II-9)

2-phenyl-1H-benzoimidazole was used as the ligand (L) to produce the title complex II-9 in according to the detailed steps described in Example 13. $^1$H NMR (CD$_3$OD, δ): 1.76 (s, 6 H), 5.32 (s, 1H), 6.21 (d, J=8.0Hz, 2 H), 6.46 (t, J=6.8 Hz, 2 H), 6.70 (t, J=7.2Hz, 2 H), 7.12 (t, J=7.2Hz, 2 H), 7.22 (t, J=7.6Hz, 2 H), 7.43 (d, J=8.0 Hz, 2 H), 7.52–7.55 (m, 4 H).

Example 23

Synthesis of Ir(Dfppb)$_2$(acac) (II-10)

Figure 10:
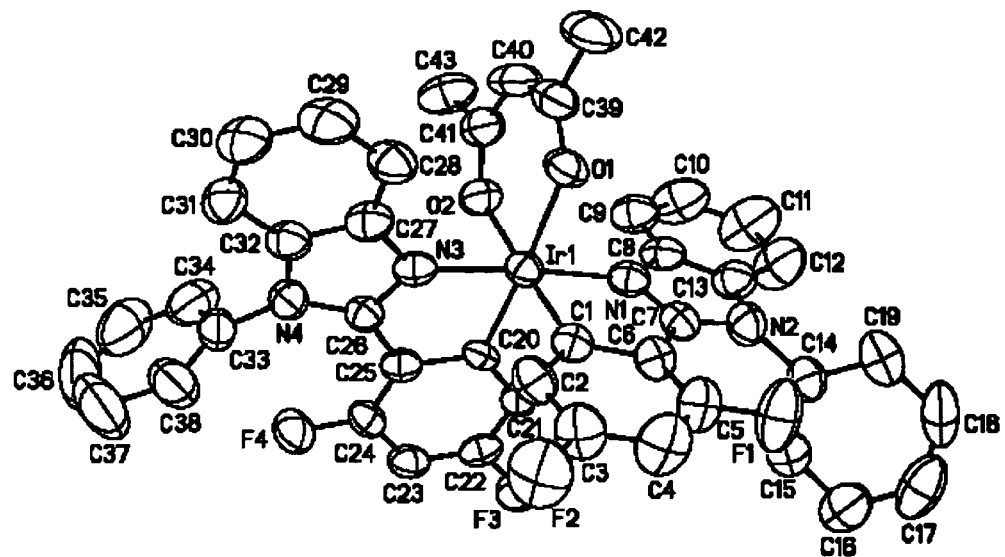
FIG. 10 represents the X-ray structure of the complex II-10.
Figure 11:
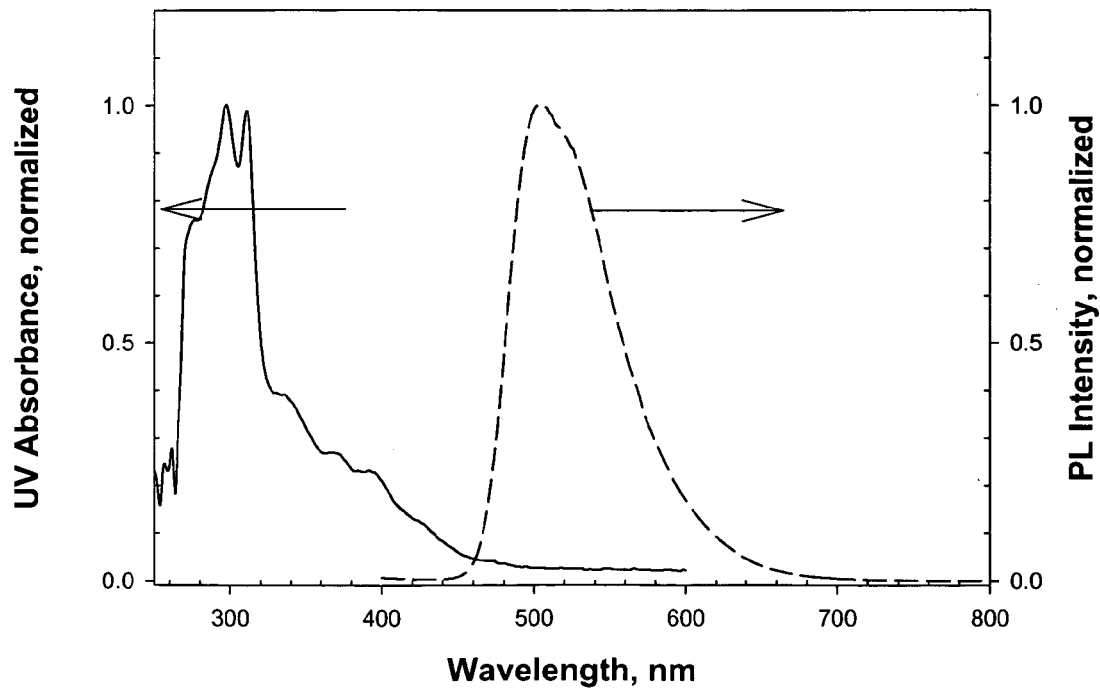
FIG. 11 represents the UV absorption spectrum (represented by the solid line, left y-axis) and the phosphorescence emission spectrum (represented by the dotted line, right y-axis) of the complex II-10 dissolved in dichloromethane.

Dfppb obtained in Example 9 was used as the ligand (L) instead of Dpb to produce the title complex II-10 in a yield of 83% according to the detailed steps described in Example 16. The X-ray structure of the complex II-10 is shown in FIG. 10. The UV absorption spectrum and the phosphorescence emission spectrum of complex II-10 in dichloromethane are shown in FIG. 11. The complex II-10 emits a green light having a peak wavelength of 502 nm. $^1$H NMR (CDCl$_3$, δ): 1.86 (s, 6 H), 5.26 (s, 1 H), 5.89–5.91 (d, J=6.0 Hz, 2 H), 6.03–6.09 (t, J=12.0 Hz, 2 H), 7.12–7.14 (m, 2 H), 7.28–7.32 (m, 4 H), 7.49–7.51 (m, 4 H), 7.58–7.60 (m, 6 H), 7.65–7.67 (m, 2 H).

Example 24

Synthesis of Ir(Fppb)$_2$(acac) (II-11)

Figure 12:
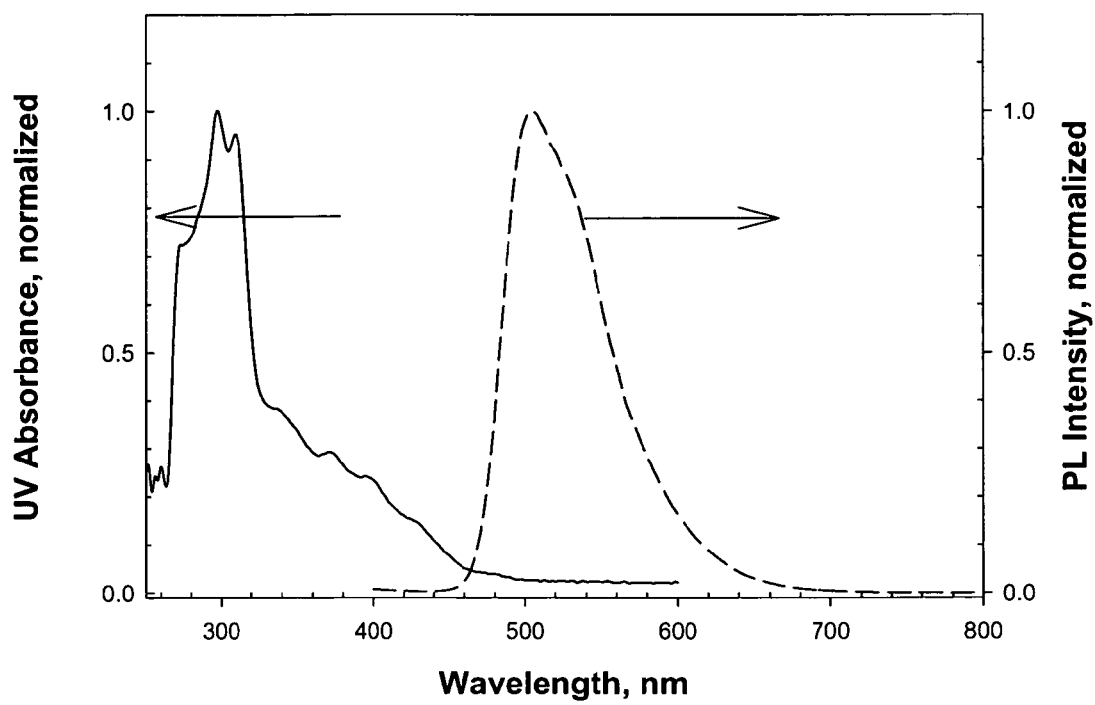
FIG. 12 represents the UV absorption spectrum (represented by the solid line, left y-axis) and the phosphorescence emission spectrum (represented by the dotted line, right y-axis) of the complex II-11 dissolved in dichloromethane.

Fppb obtained in Example 10 was used as the ligand (L) instead of Dpb to produce the title complex II-11 in a yield of 74% according to the detailed steps described in Example 16. The UV absorption spectrum and the phosphorescence emission spectrum of the complex II-11 in dichloromethane are shown in FIG. 12. The complex II-11 emits a green light having a peak wavelength of 504 nm. $^1$H NMR (CDCl$_3$, δ): 1.86 (s, 6 H), 5.26 (s, 1 H), 6.08 (dd, J=10.0 Hz, J=2.0 Hz, 2 H), 6.20 (t, J=6.0 Hz, 2 H), 6.53 (dd, J=8.0 Hz, J=5.0 Hz, 2 H), 7.10–7.12 (m, 2 H), 7.26–7.30 (m, 4 H), 7.59–7.70 (m, 12 H).

Example 25

Synthesis of Ir(Ptpb)$_2$(acac) (II-12)

Figure 13:
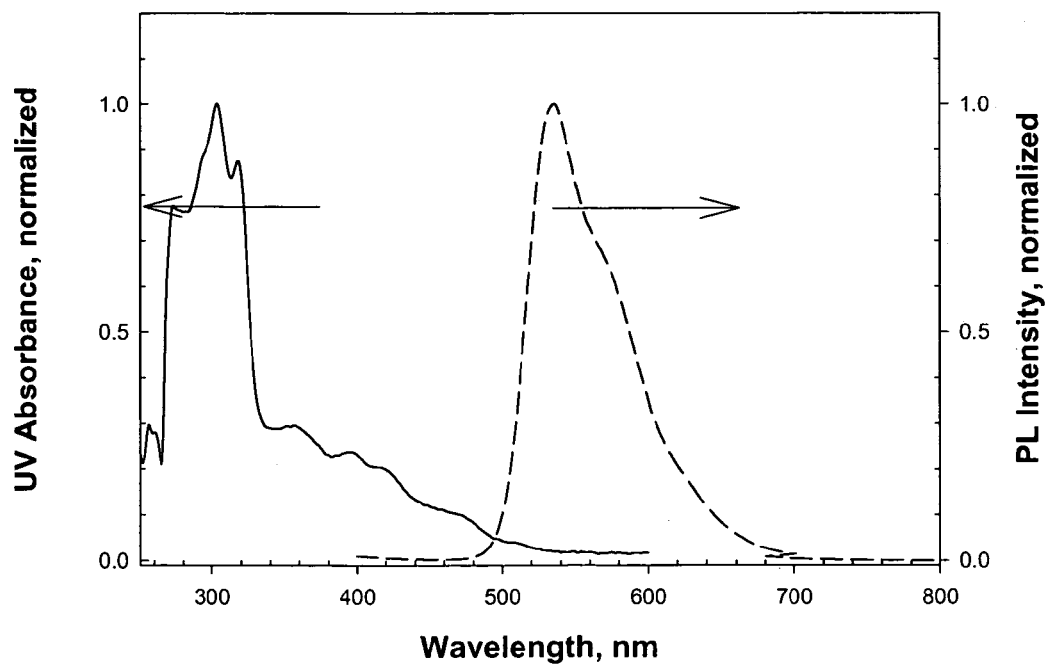
FIG. 13 represents the UV absorption spectrum (represented by the solid line, left y-axis) and the phosphorescence emission spectrum (represented by the dotted line, right y-axis) of the complex II-12 dissolved in dichloromethane.

Ptpb obtained in Example 11 was used as the ligand (L) instead of Dpb to produce the complex II-12 in a yield of 92% according to the detailed steps described in Example 16. The UV absorption spectrum and the phosphorescence emission spectrum of the complex II-12 in dichloromethane are shown in FIG. 13. The complex II-12 emits a green light having a peak wavelength of 536 nm. $^1$H NMR (CDCl$_3$, δ): 1.87 (s, 6 H), 5.31 (s, 1 H), 6.54–6.58 (m, 4 H), 6.69–6.71 (m, 2 H), 7.14–7.16 (m, 2 H), 7.33–7.35 (m, 4 H), 7.49–7.51 (m, 2 H), 7.63–7.70 (m, 10 H).

Example 26

Synthesis of Ir(Bdmpb)$_2$(acac) (II-13)

Figure 14:
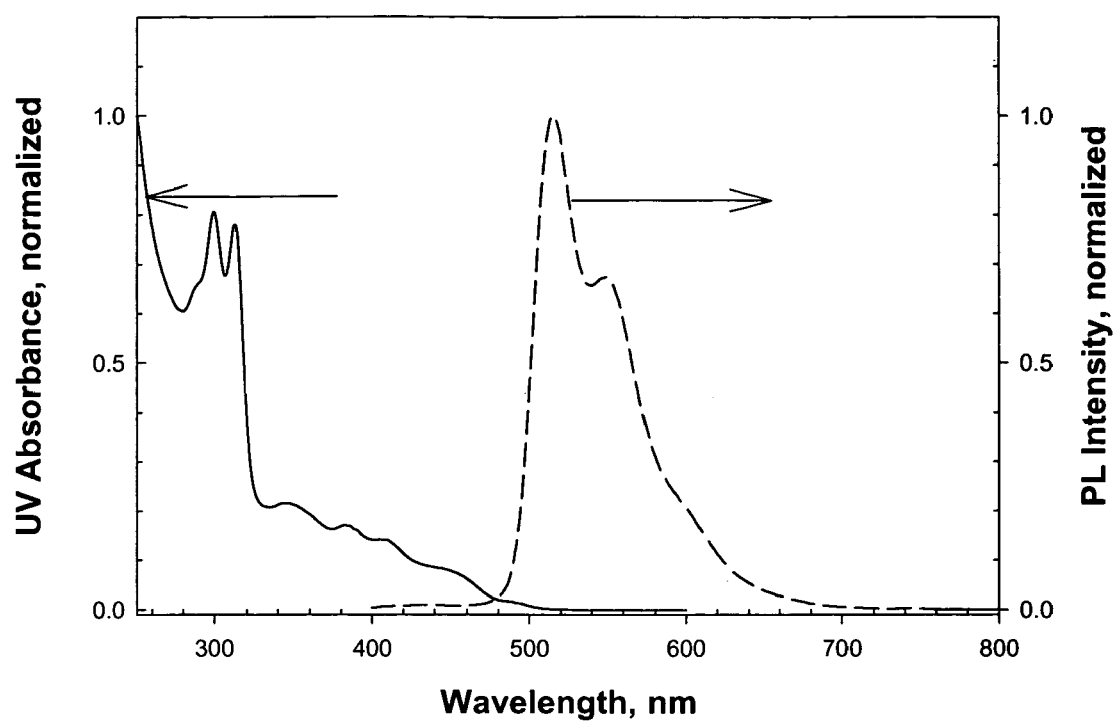
FIG. 14 represents the UV absorption spectrum (represented by the solid line, left y-axis) and the phosphorescence emission spectrum (represented by the dotted line, right y-axis) of the complex II-13 dissolved in dichloromethane.

Bdmpb obtained in Example 12 was used as the ligand (L) to produce the title complex II-13 in a yield of 83% according to the detailed steps described in Example 13. The UV absorption spectrum and the phosphorescence emission spectrum of the complex II-13 in dichloromethane are shown in FIG. 14. The complex II-11 emits a green light having a peak wavelength of 514 nm. $^1$H NMR (CDCl$_3$, δ): 1.80 (s, 6 H), 2.30 (s, 6 H), 2.34 (s, 6 H), 5.18 (s, 1 H), 5.86 (dd, J=16.3 Hz, J=14.0 Hz, 4 H), 6.44 (d, J=7.6 Hz, 2 H), 6.51 (t, J=7.6 Hz, 2 H), 6.61 (t, J=7.2 Hz, 2 H), 7.11 (s, 2 H), 7.21–7.37 (m, 12 H), 7.50 (s, 2 H).

Examples of Organic Light Emitting Diode Devices

During the formation of OLED devices, organic materials, phosphorescent iridium complexes, and metal were deposited in a chamber at $5\times10^{-6'}$ torr at a deposition rate of about 1.5–2.5 angstroms per second for the organic materials, at a deposition rate of about 0.05–0.2 angstroms per second for the phosphorescent iridium complexes, and at a deposition rate of about 0.5 angstroms per second for the potassium fluoride. In certain embodiments, a hole injection modification layer has a thickness ranging from about 10 to about 35 nanometers. In certain embodiments, a hole transporting layer has a thickness ranging from about 10 to about 50 nanometers. In certain embodiments, a hole blocking layer has a thickness ranging from about 10 to about 20 nanometers. In certain embodiments, a electron transporting layer has a thickness ranging from about 10 to about 50 nanometers. In certain embodiments, an election injection layer such as potassium fluoride, has a thickness of about 0.5 nanometer. When the cathode was made of Mg/Ag alloy, the Mg deposition rate was about 5 angstroms per second, and the Ag deposition rate was about 0.5 angstrom per second wherein Mg and Ag were co-evaporated at a ratio of 10:1. In certain embodiments, when the cathode was made of Ca/Mg, the deposition rate was about 5 angstroms per second, and the thickness of the deposited cathode layer ranged from about 10 to about 55 nanometers. In certain embodiments, when silver was deposited and aromatic amine (such as 2-TNATA or IDE320 was deposited as a protection layer, the layer had a thickness ranging from about 30 to about 150 nanometers. Certain device configurations are set forth in Examples 25–51, and corresponding characteristics are provided in Table 1. In Examples 27–51, the composition and thickness of the layers comprising a device are provided in the following order: anode layer//hole injection layer//light emitting layer//hole blocking layer// electron transport layer//and cathode layer.

Example 27

ITO//NPB (50 nm)//II-1: CBP (4.3 %, 30 nm)//BCP (10 nm)//Alq (40 nm)//Mg:Ag(10:1).

Example 28

ITO//NPB (50 nm)//II-1: CBP (7.3%, 30 nm)//BCP (10 nm)//Alq (40 nm)//Mg:Ag=10:1.

Example 29

ITO//NPB (50 nm)//II-1: TCTA (6.3%, 30 nm)//BCP (10 nm)//Alq (40 nm)//Mg:Ag=10:1.

Example 30

ITO//TCTA (30 nm)//II-1: TCTA (6.3%, 30 nm)//BCP (10 nm)//Alq (40 nm)//Mg:Ag=10:1.

Example 31

ITO//NPB (30 nm)//II-2: CBP (7.3%, 30 nm)//BCP (10 nm)//Alq.(40 nm)//Mg:Ag=10:1.

Example 32

ITO//TCTA (30 nm)//II-2: CBP (7%, 30 nm)//BCP (10 nm)//Alq (40 nm)//Mg:Ag=10:1.

Example 33

ITO//NPB (50 nm)//II-3: CBP (7%, 30 nm)//BCP (10 nm)//Alq (40 nm)//Mg:Ag=10:1.

Example 34

ITO//NPB (30 nm)//II-3: CBP (9%, 30 nm)//BCP (10 nm)//Alq (40 nm)//Mg:Ag=10:1.

Example 35

ITO//TCTA (30 nm)//II-3: TCTA (6.7%, 30 nm)//BCP (10 nm)//Alq (40 nm)//Mg:Ag=10:1.

Example 36

ITO//TCTA (30 nm)//II-3: CBP (6.3%, 30 nm)//BCP (10 nm)//Alq (40 nm)//Mg:Ag=10:1.

Example 37

ITO//TCTA (30 nm)//II-3: TCB (6.7%, 30 nm)//BCP (10 nm)//Alq (40 nm)//Mg:Ag=10:1

Example 38

ITO//CuPc (10 nm)//NPB (30 nm)//II-3: CBP (5.7%, 30 nm)//BCP (10 nm)//Alq (40 nm)//Mg:Ag=10:1.

Example 39

ITO//TCTA (30 nm)//II-3: CBP (7%, 30 nm)//BAlq (30 nm)//Mg:Ag=10:1.

Example 40

Al/Ni/NiO//IDE406 (35 nm)//IDE320 (10 nm)//II-3: TMM004 (7%, 25 nm)//BAlq (10 nm)//TYE704 (20 nm)//Ca (15 nm)//Mg (8 nm)//IDE320 (50 nm).

Example 41

ITO//NPB (50 nm)//II-4: CBP (4.7%, 30 nm)//BCP (10 nm)//Alq (40 nm)//Mg:Ag=10:1.

Example 42

ITO//NPB (50 nm)//II-4: CBP (6.7%, 30 nm)//BCP (10 nm)//Alq (40 nm)//Mg:Ag=10:1.

Example 43

ITO//NPB (50 nm)//II-4: CBP (8.7%, 30 nm)//BCP (10 nm)//Alq (40 nm)//Mg:Ag=10:1.

Example 44

ITO//NPB (50 nm)//II-4: TCTA (7%, 30 nm)//BCP (10 nm)//Alq (40 nm)//Mg:Ag=10:1.

Example 45

ITO//NPB (30 nm)//TCTA (20 nm)//II-4: TCTA (7%, 30 nm)//BCP (10 nm)//Alq (40 nm)//Mg:Ag=10:1.

Example 46

ITO//NPB (30 nm)//II-5: CCP (9.7%, 30 nm)//BCP (10 nm)//Alq (40 nm)//Mg:Ag=10:1.

Example 47

ITO//m-MTDATA (30 nm)//II-5: CCP (10.3%, 30 nm)//BCP (10 nm)//Alq (40 nm)//Mg:Ag=10:1.

Example 48

ITO//TCTA (30 nm)//II-5: TCB (6.3%, 30 nm)//BCP (10 nm)//Alq (40 nm)//Mg:Ag=10:1.

Example 49

ITO//TCTA (30 nm)//II-10: CBP (7%, 30 nm)//BCP (10 nm)//Alq (40 nm)//Mg:Ag=10:1.

Example 50

ITO//TCTA (30 nm)//II-11: CBP (6.7%, 30 nm)//BCP (10 nm)//Alq (40 nm)//Mg:Ag=10:1.

Example 51

ITO//NPB (50 nm)//II-13: CBP (7%, 30 nm)//BCP (10 nm)//Alq (40 nm)//Mg:Ag=10:1.

TABLE 1

| Example | Voltage (V) | External Quantum Efficiency (%) | Maximum Brightness (cd/m² (V)) | Peak Efficiency (cd/A (V)) | CIE Coordinates (8 V) (x, y) | Peak Wavelength $\lambda_{max}$ (nm) |
|---|---|---|---|---|---|---|
| 27 | 3.1 | 11.10 (7.5) | 100126 (14.0) | 40.85 (7.5) | (0.24, 0.66) | 512 |
| 28 | 2.9 | 9.38 (8.0) | 98799 (13.0) | 35.29 (8.0) | (0.27, 0.64) | 514 |
| 29 | 2.8 | 10.66 (6.0) | 89343 (13.0) | 39.59 (6.0) | (0.26, 0.65) | 512 |
| 30 | 2.7 | 9.14 (6.5) | 72045 (12.5) | 33.73 (6.5) | (0.26, 0.64) | 512 |
| 31 | 3.0 | 9.54 (6.5) | 101622 (13.0) | 35.89 (6.5) | (0.27, 0.65) | 514 |
| 32 | 2.7 | 7.88 (7.5) | 105202 (13.0) | 29.58 (7.5) | (0.28, 0.64) | 514 |
| 33 | 3.0 | 14.69 (6.0) | 140407 (14.5) | 57.44 (6.0) | (0.30, 0.64) | 520 |
| 34 | 2.7 | 11.71 (6.5) | 130455 (13.5) | 45.29 (6.5) | (0.31, 0.63) | 520 |
| 35 | 2.7 | 7.58 (5.5) | 65773 (11.5) | 29.21 (5.5) | (0.29, 0.64) | 520 |
| 36 | 3.0 | 10.50 (7.0) | 143374 (13.5) | 41.17 (7.0) | (0.31, 0.64) | 522 |
| 37 | 2.7 | 13.46 (7.5) | 136208 (14.5) | 52.61 (7.5) | (0.31, 0.64) | 522 |
| 38 | 3.5 | 15.53 (7.5) | 119615 (17.5) | 61.77 (7.5) | (0.30, 0.65) | 522 |
| 39 | 4.5 | 4.54 (8.5) | 66466 (13.5) | 17.77 (8.5) | (0.32, 0.63) | 520 |
| 40 | 2.5 | 15.86 (3.5) | 56140 (10.0) | 63.11 (3.5) | (0.35, 0.61) | 525 |
| 41 | 3.0 | 11.02 (8.0) | 88080 (14.5) | 42.10 (8.0) | (0.29, 0.64) | 516 |
| 42 | 2.8 | 14.02 (7.5) | 114309 (14.0) | 54.73 (7.5) | (0.30, 0.64) | 518 |
| 43 | 2.8 | 11.89 (8.5) | 104291 (14.0) | 46.10 (8.5) | (0.29, 0.65) | 516 |
| 44 | 2.7 | 10.15 (5.5) | 62776 (12.0) | 38.52 (5.5) | (0.27, 0.65) | 514 |
| 45 | 3.1 | 9.61 (7.5) | 70540 (12.5) | 36.76 (7.5) | (0.28, 0.65) | 516 |
| 46 | 3.9 | 3.77 (8.0) | 17614 (12.5) | 12.61 (8.0) | (0.26, 0.57) | 496 |
| 47 | 4.1 | 4.73 (8.5) | 16769 (15.5) | 15.74 (8.5) | (0.24, 0.57) | 496 |
| 48 | 3.7 | 5.04 (8.0) | 19111 (12.5) | 16.29 (8.0) | (0.23, 0.57) | 494 |
| 49 | 4.5 | 4.29 (8.5) | 13610 (12.0) | 13.72 (8.5) | (0.23, 0.58) | 498 |
| 50 | 3.7 | 10.44 (9.0) | 47584 (13.0) | 34.91 (9.0) | (0.23, 0.60) | 502 |
| 51 | 2.8 | 9.37 (8.0) | 58180 (13.2) | 36.89 (8.0) | (0.31, 0.64) | 520 |

As is apparent from the results given in Table 1, the phosphorescent iridium complexes disclosed in the present disclosure are suitable for use in forming an OLED device. An OLED device formed using the phosphorescent iridium complexes of the present disclosure can emit light having a color ranging from blue-green through green, high brightness, high current efficiency, and excellent CIE coordinates. A wavelength ranging from about 470 nm to about 570 nm corresponds to the blue-green to green region of the electromagnetic spectrum. In certain embodiments, an OLED device comprising at least one phosphorescent iridium complex of the disclosure emits light having a peak wavelength ranging from about 490 nm to 530 mn.

Other embodiments of the present disclosure will be apparent to those skilled in the art from consideration of the specification and practice of the invention as disclosed herein. It is intended that the specification and examples be considered as exemplary only, with a true scope and spirit of the present disclosure being indicated by the following claims.

The invention claimed is:

1. An organic light emitting diode device, comprising:
an anode and a cathode; and
an electroluminescent medium disposed between the anode and the cathode,
wherein the electroluminescent medium comprises a light-emitting layer comprising a phosphorescent iridium complex of Formula (I) or Formula (II):

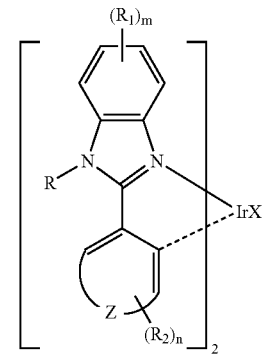

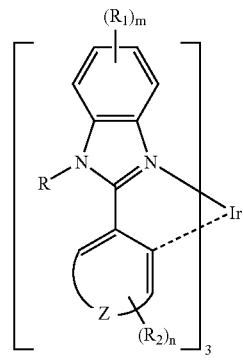

wherein:
X is chosen from a monoanionic bidentate ligand;

Z is chosen from an atomic group wherein Z together with the buta-1,3-diene to which Z is attached form an aryl group or a heteroaryl group;

R is chosen from $C_2$–$C_{20}$ alkyl, $C_2$–$C_{20}$ alkenyl, $C_2$–$C_{20}$ alkynyl, halogen-substituted $C_2$–$C_{20}$ alkyl, $C_1$–$C_{20}$ alkoxy, $C_1$–$C_{20}$ alkyl substituted amino, $C_1$–$C_{20}$ acyl, $C_1$–$C_{20}$ ester, $C_1$–$C_{20}$ amide, halogen-substituted alkenyl, haloalkyl-substituted alkenyl, and aryl-substituted $C_1$–$C_{20}$ alkyl;

$R_1$ and $R_2$ are independently chosen from H, halogen, $C_1$–$C_{20}$ alkyl, $C_2$–$C_{20}$ alkenyl, $C_2$–$C_{20}$ alkynyl, halogen-substituted $C_1$–$C_{20}$ alkyl, $C_1$–$C_{20}$ alkoxy, $C_1$–$C_{20}$ alkyl substituted amino, $C_1$–$C_{20}$ acyl, $C_1$–$C_{20}$ ester, $C_1$–$C_{20}$ amide, aryl, halogen-substituted aryl, halogen-substituted alkenyl, haloalkyl-substituted aryl, haloalkyl-substituted alkenyl, aryl-substituted $C_1$–$C_{20}$ alkyl, cyano, and nitro;

m is an integer from 0 to 4; and n is an integer from 0 to the maximum number of possible substituents on Z.

2. The organic light emitting diode device of claim 1, wherein Z together with the buta-1,3-diene group to which Z is attached form an aryl group chosen from phenyl, naphthyl, diphenyl, anthryl, pyrenyl, phenanthryl, and fluorene.

3. The organic light emitting diode device of claim 1, wherein Z together with the buta-1,3-diene group to which Z is attached form a heteroaryl chosen from benzofuran, thiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, and phenanthroline.

4. The organic light emitting diode device of claim 1, wherein X is chosen from acetylacetonate, an amino acid anion, salicylaldehyde anion, 2-picolinate, 8-hydroxyquinoline anion, and iminoacetonate.

5. The organic light emitting diode device of claim 1, wherein X is acetylacetonate.

6. The organic light emitting diode device of claim 1, wherein R is chosen from aryl-substituted $C_1$–$C_{20}$ alkyl, haloalkyl-substituted alkenyl, $C_2$–$C_{20}$ alkyl, and halogen-substituted alkenyl.

7. The organic light emitting diode device of claim 6, wherein $R_1$ is chosen from H, and $C_1$–$C_{20}$ alkyl.

8. The organic light emitting diode device of any one of claims 6–7, wherein $R_2$ is chosen from H, halogen, $C_1$–$C_{20}$ alkyl, halogen-substituted $C_1$–$C_{20}$ alkyl, and $C_1$–$C_{20}$ alkoxy.

9. The organic light emitting diode device of claim 1, wherein, when a voltage is applied between the anode and the cathode, the light-emitting layer emits light having a peak wavelength ranging from 470 nm to 570 nm.

10. The organic light emitting diode device of claim 1, wherein the light-emitting layer further comprises a host material and the phosphorescent iridium complex resides as a dopant in the host material.

11. The organic light emitting diode device of claim 10, wherein the host material comprises a hole-transporting material.

12. The organic light emitting diode device of claim 10, wherein the host material comprises an electron-transporting material.

13. The organic light emitting diode device of claim 11, wherein the hole-transporting material comprises the compound of Formula (III):

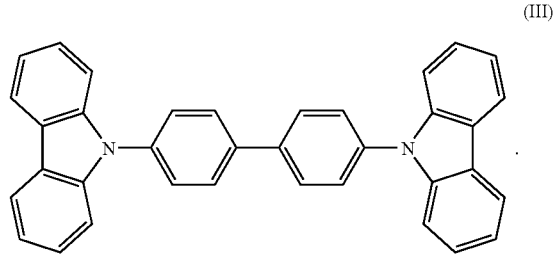

(III)

14. The organic light emitting diode device of claim 11, wherein the hole-transporting material comprises the compound of Formula (IV):

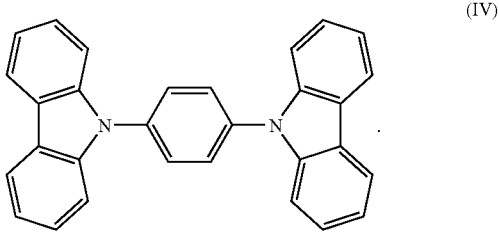

(IV)

15. The organic light emitting diode device of claim 11, wherein the hole-transporting material comprises a compound of Formula (V):

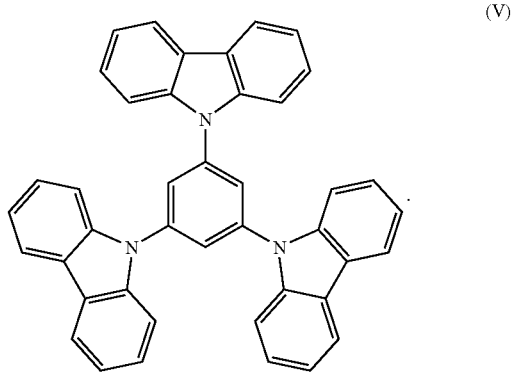

(V)

16. The organic light emitting diode device of claim 11, wherein the hole-transporting material comprises a compound of Formula (VI):

17. The organic light emitting diode device of claim 12, wherein the electron-transporting material comprises a compound of Formula (VII):

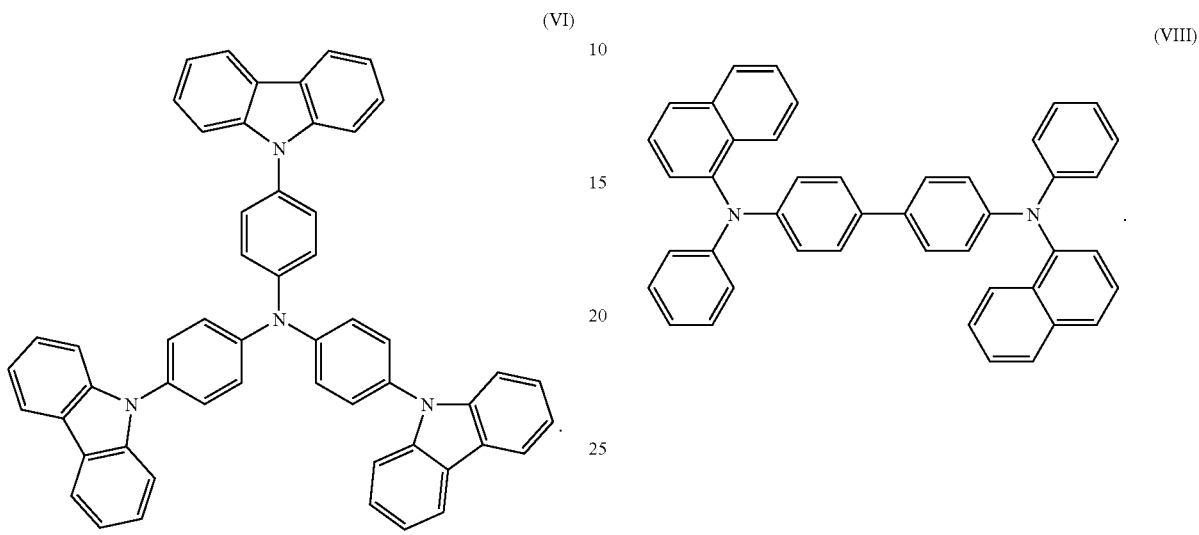

18. The organic light emitting diode device of claim 1, wherein the electroluminescent medium further comprises a hole transporting layer disposed between the anode and the light-emitting layer.

19. The organic light emitting diode device of claim 18, wherein the hole transporting layer comprises a compound of Formula (VIII):

20. The organic light emitting diode device of claim 18, wherein the hole transporting layer comprises a compound of Formula (IX):

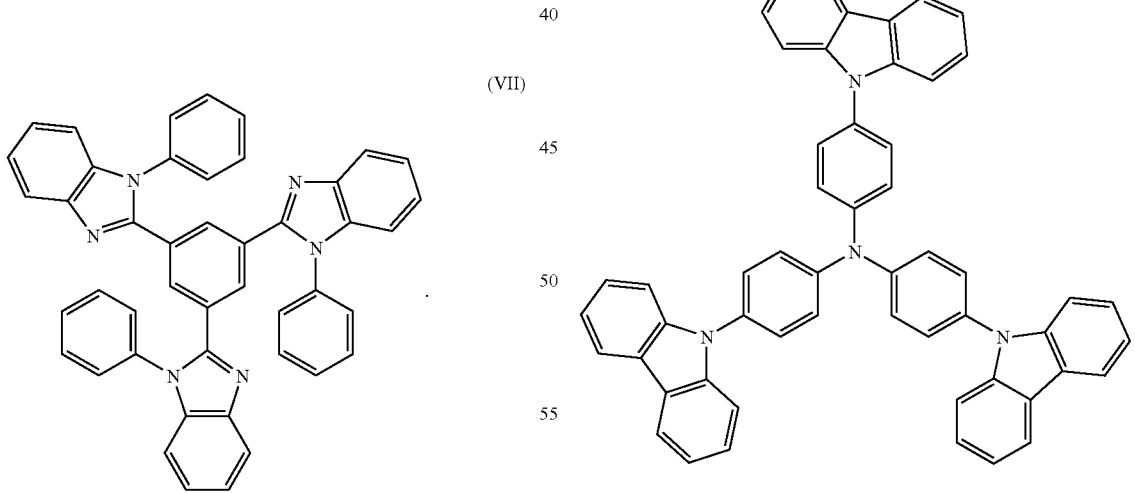

21. The organic light emitting diode device of claim 18, wherein the electroluminescent medium further comprises a hole injection modification layer disposed between the anode and the hole transporting layer.

22. The organic light emitting diode device of claim 21, wherein the hole injection modification layer comprises a compound of Formula (X):

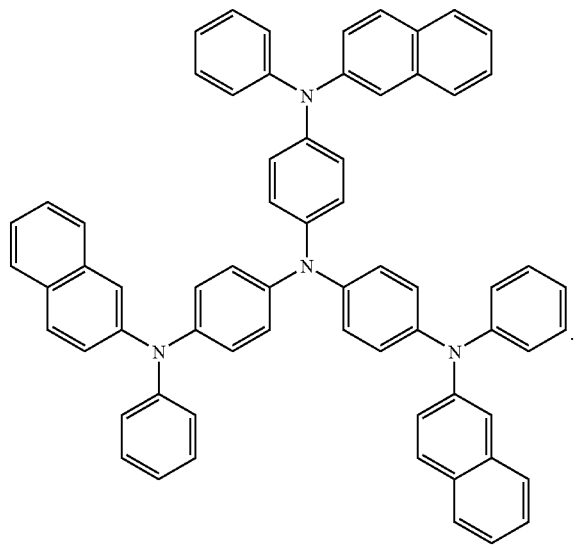

(X)

23. The organic light emitting diode device of claim 21, wherein the hole injection modification layer comprises a compound of Formula (XI):

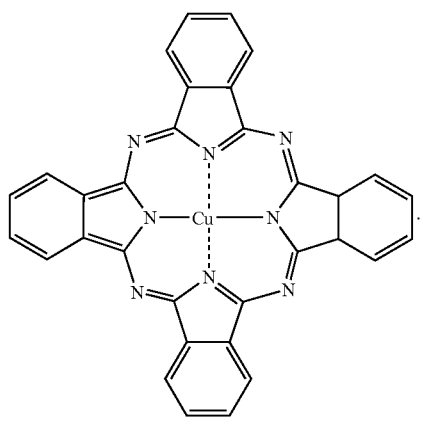

(XI)

24. The organic light emitting diode device of claim 1, wherein the electroluminescent medium further comprises a hole-blocking layer disposed between the cathode and the light-emitting layer, wherein the hole-blocking layer contacts the light-emitting layer.

25. The organic light emitting diode device of claim 24, wherein the hole-blocking layer comprises a compound of Formula (XII):

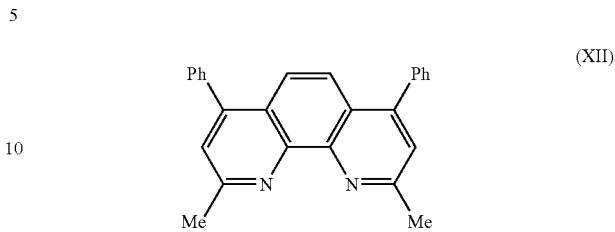

(XII)

wherein Ph represents a phenyl group, and Me represents a methyl group.

26. The organic light emitting diode device of claim 24, wherein the hole-blocking layer comprises a compound of Formula (XIII):

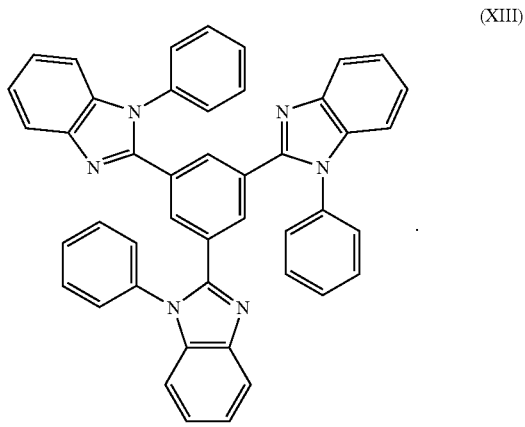

(XIII)

27. The organic light emitting diode device of claim 24, wherein the hole-blocking layer comprises a compound of Formula (XIV):

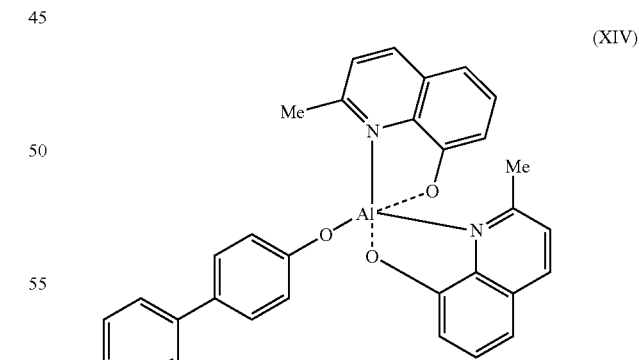

(XIV)

wherein Me represents a methyl group.

28. The organic light emitting diode device of claim 24, wherein the electroluminescent medium further comprises an electron transporting layer disposed between the hole-blocking layer and the cathode.

29. The organic light emitting diode device of claim 28, wherein the electron transporting layer comprises a compound of Formula (XV):

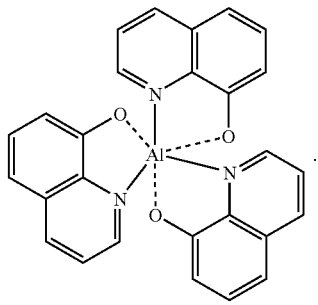
(XV)

30. A light-emitting material comprising a compound of Formula (I) or Formula (II):

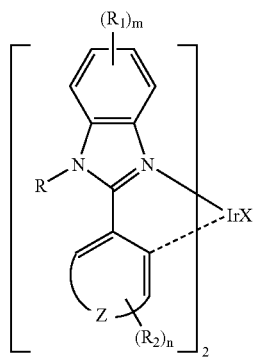
I

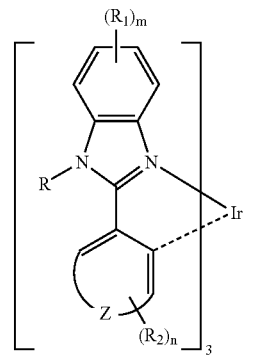
II wherein:
X is chosen from a monoanionic bidentate ligand;
Z is chosen from an atomic group wherein Z together with the buta-1,3-diene to which Z is attached form an aryl group or a heteroaryl group;
R is chosen from $C_2$–$C_{20}$ alkyl, $C_2$–$C_{20}$ alkenyl, $C_2$–$C_{20}$ alkynyl, halogen-substituted $C_2$–$C_{20}$ alkyl, $C_1$–$C_{20}$ alkoxy, $C_1$–$C_{20}$ alkyl substituted amino, $C_1$–$C_{20}$ acyl, $C_1$–$C_{20}$ ester, $C_1$–$C_{20}$ amide, halogen-substituted alkenyl, haloalkyl-substituted alkenyl, and aryl-substituted $C_1$–$C_{20}$ alkyl;
$R_1$ and $R_2$ are independently chosen from H, halogen, $C_1$–$C_{20}$ alkyl, $C_2$–$C_{20}$ alkenyl, $C_2$–$C_{20}$ alkynyl, halogen-substituted $C_1$–$C_{20}$ alkyl, $C_1$–$C_{20}$ alkoxy, $C_1$–$C_{20}$ alkyl substituted amino, $C_1$–$C_{20}$ acyl, $C_1$–$C_{20}$ ester, $C_1$–$C_{20}$ amide, aryl, halogen-substituted aryl, halogen-substituted alkenyl, haloalkyl-substituted aryl, haloalkyl-substituted alkenyl, aryl-substituted $C_1$–$C_{20}$ alkyl, cyano, and nitro;
m is an integer from 0 to 4; and
n is an integer from 0 to the maximum number of possible substituents on Z.

31. The light-emitting material of claim 30, wherein Z together with the buta-1,3-diene group to which Z is attached form an aryl group chosen from phenyl, naphthyl, diphenyl, anthryl, pyrenyl, phenanthryl, and fluorene.

32. The light-emitting material of claim 30, wherein Z together with the buta-1,3-diene group to which Z is attached form a heteroaryl group chosen from benzofuran, thiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, and phenanthroline.

33. The light-emitting material of claim 30, wherein X is chosen from acetylacetonate, an amino acid anion, salicylaldehyde anion, 2-picolinate, 8-hydroxyquinoline anion, and iminoacetonate.

34. The light-emitting material of claim 30, wherein X is acetylacetonate.

35. The light-emitting material of claim 30, wherein R is chosen from aryl-substituted $C_1$–$C_{20}$ alkyl, haloalkyl-substituted alkenyl, $C_2$–$C_{20}$ alkyl, and halogen-substituted alkenyl.

36. The light-emitting material of claim 35, wherein $R_1$ is chosen from H, and $C_1$–$C_{20}$ alkyl.

37. The light-emitting material of any one of claims 35–36, wherein $R_2$ is chosen from H, halogen, $C_1$–$C_{20}$ alkyl, halogen-substituted $C_1$–$C_{20}$ alkyl, and $C_1$–$C_{20}$ alkoxy.

38. The light-emitting material of claim 30, wherein the compound is chosen from Formula II-2, II-4, II-5, II-6, II-7, II-8, and II-13:

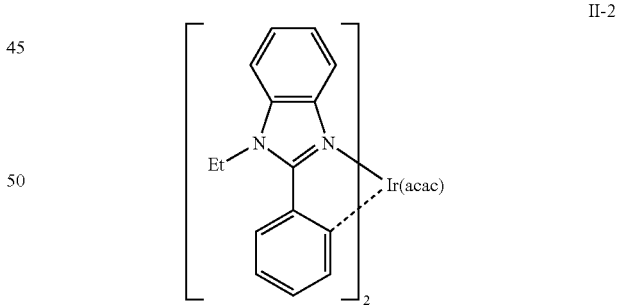
II-2

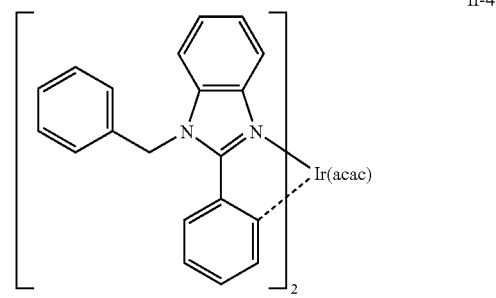
II-4

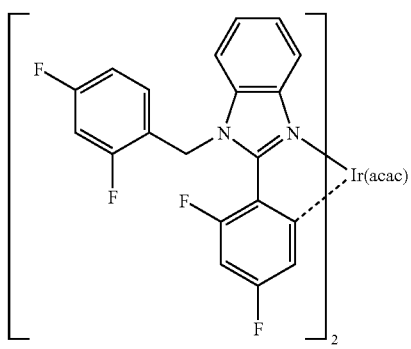
II-5
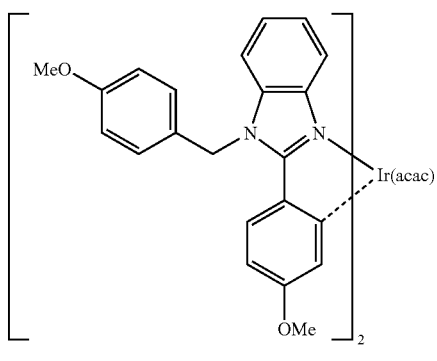
II-6
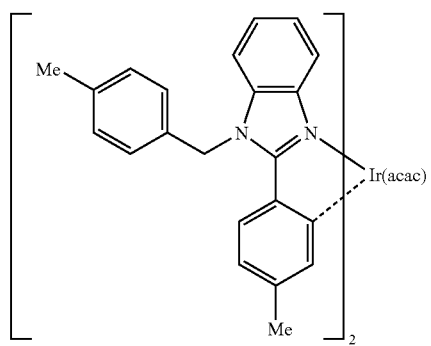
II-7
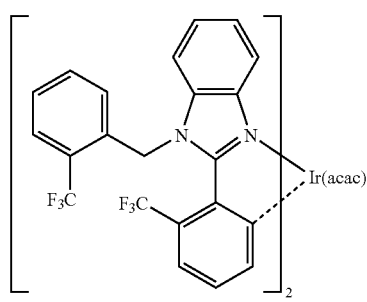
II-8
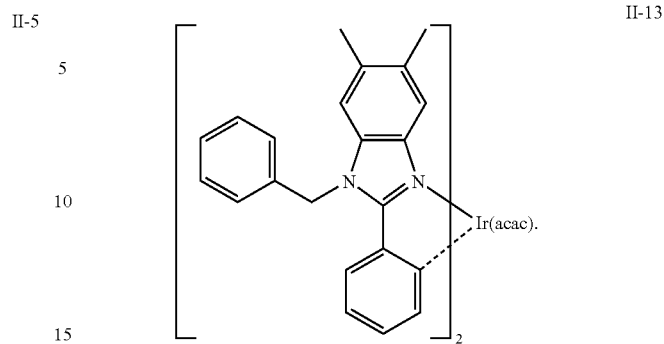
II-13
39. The organic light emitting diode device of claim 1, wherein the light-emitting layer comprises at least one compound chosen from Formula II-2, II-4, II-5, II-6, II-7, II-8, and II-13:
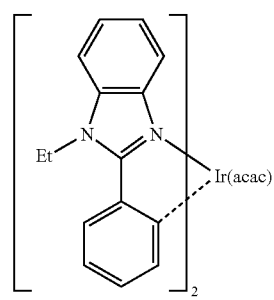
II-2
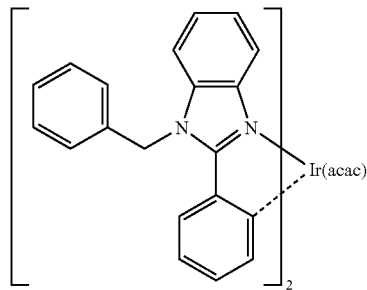
II-4
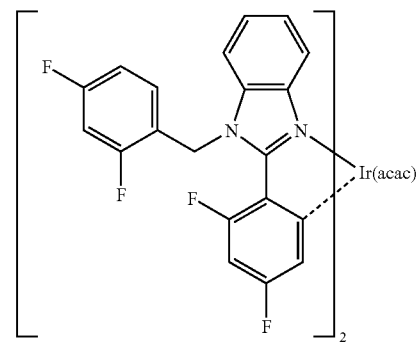
II-5

-continued
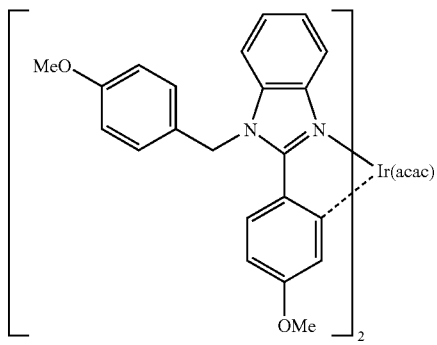
II-6
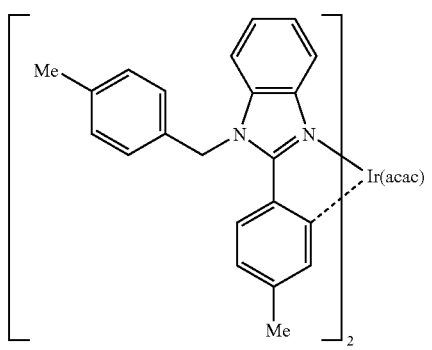
II-7
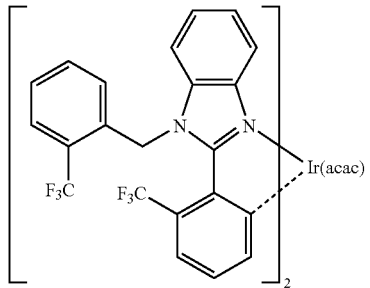
II-8
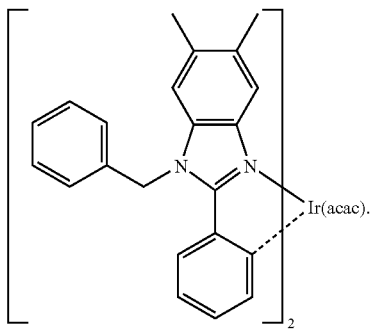
II-13
* * * * *